(12) United States Patent
Hyde et al.

(10) Patent No.: US 9,772,270 B2
(45) Date of Patent: Sep. 26, 2017

(54) DEVICES AND METHODS FOR RECORDING INFORMATION ON A SUBJECT'S BODY

(75) Inventors: Roderick A. Hyde, Redmond, WA (US); Jordin T. Kare, Seattle, WA (US)

(73) Assignee: Elwha LLC, Bellevue, WA (US)

( * ) Notice: Subject to any disclaimer, the term of this patent is extended or adjusted under 35 U.S.C. 154(b) by 14 days.

(21) Appl. No.: 13/587,029

(22) Filed: Aug. 16, 2012

(65) Prior Publication Data
US 2013/0046227 A1 Feb. 21, 2013

Related U.S. Application Data

(63) Continuation-in-part of application No. 13/199,038, filed on Aug. 16, 2011, now abandoned, and a
(Continued)

(51) Int. Cl.
*G06Q 50/00* (2012.01)
*G01N 15/02* (2006.01)
(Continued)

(52) U.S. Cl.
CPC ....... *G01N 15/0205* (2013.01); *G06F 19/322* (2013.01); *G06F 19/3418* (2013.01);
(Continued)

(58) Field of Classification Search
CPC ........ G06C 50/22; G06C 50/24; G06C 40/08; G06C 10/10; G06F 19/322
See application file for complete search history.

(56) References Cited

U.S. PATENT DOCUMENTS 4,315,246 A 2/1982 Milford
5,201,715 A 4/1993 Masters
(Continued)

OTHER PUBLICATIONS

Belongie, Serge et al., "Shape Matching and Object Recognition Using Shape Contexts", IEEE Transactions on Pattern Analysis and Machine Intelligence, Apr. 2002, pp. 509-510, vol. 24, No. 24, IEEE.
(Continued)

*Primary Examiner* — Tran Nguyen

(57) ABSTRACT

Embodiments disclosed herein relate to methods, devices, and computer systems thereof for visibly or non-visibly indicating a subject has received a medical treatment. In certain embodiments, a subject receives an information mark in conjunction with a medical treatment. In certain embodiments, the information mark includes unique information relating to the subject. In certain embodiments, the information mark is fluorescent or phosphorescent. In certain embodiments, the information mark includes one or more magnetic particles. In certain embodiments, the information mark includes a combination of magnetic particles, fluorescent particles, phosphorescent particles, and/or multi-spectral ink. In certain embodiments, devices, computer systems, and methods relate to reading an information mark on a subject, and optionally determining if further medical treatment of the subject is warranted. In certain embodiments, receipt of an information mark entitles a subject to a reward.

12 Claims, 7 Drawing Sheets

M T W Th Fr Sa Su

Green Dots (propranolol)

Brown Ovals (hydrochlorothiazide)

Related U.S. Application Data continuation-in-part of application No. 13/199,046, filed on Aug. 16, 2011, now Pat. No. 9,443,061, and a continuation-in-part of application No. 13/199,047, filed on Aug. 16, 2011, now Pat. No. 9,286,615, and a continuation-in-part of application No. 13/474,995, filed on May 18, 2012.

(51) Int. Cl.
| | | |
|---|---|---|
| *G06Q 50/22* | (2012.01) | |
| *G06F 19/00* | (2011.01) | |
| *G06Q 10/10* | (2012.01) | |
| *G06Q 10/00* | (2012.01) | |
| *A61M 5/20* | (2006.01) | |
| *A61M 5/31* | (2006.01) | |
| *A61M 15/00* | (2006.01) | |
| *A61M 37/00* | (2006.01) | |

(52) U.S. Cl.
CPC ......... *G06F 19/3456* (2013.01); *G06Q 10/10* (2013.01); *G06Q 50/22* (2013.01); *A61M 5/20* (2013.01); *A61M 5/3129* (2013.01); *A61M 15/00* (2013.01); *A61M 37/00* (2013.01); *A61M 2205/502* (2013.01); *A61M 2205/6009* (2013.01); *G06F 19/328* (2013.01)

(56) References Cited

U.S. PATENT DOCUMENTS

| | | |
|---|---|---|
| 5,454,045 A | 9/1995 | Perkins et al. |
| 5,772,671 A | 6/1998 | Harmon |
| 5,773,811 A | 6/1998 | Schramm, Jr. et al. |
| 5,878,155 A | 3/1999 | Heeter |
| 5,943,160 A | 8/1999 | Downing |
| 5,956,172 A | 9/1999 | Downing |
| 6,013,122 A | 1/2000 | Klitzman et al. |
| 6,100,804 A | 8/2000 | Brady et al. |
| 6,192,890 B1 | 2/2001 | Levy et al. |
| 6,228,055 B1 | 5/2001 | Foerster et al. |
| 6,234,964 B1 | 5/2001 | Iliff |
| 6,327,074 B1 | 12/2001 | Bass et al. |
| 6,350,244 B1 | 2/2002 | Fisher |
| 6,425,764 B1 | 7/2002 | Lamson |
| 6,470,891 B2 | 10/2002 | Carroll |
| 6,526,984 B1 | 3/2003 | Nilsson et al. |
| 6,558,352 B1 | 5/2003 | Hogan |
| 6,565,532 B1 | 5/2003 | Yuzhakov et al. |
| 6,699,188 B2* | 3/2004 | Wessel .................. 600/300 |
| 6,731,111 B2* | 5/2004 | Sawa ............. G08B 13/2408 194/213 |
| 6,800,122 B2 | 10/2004 | Anderson et al. |
| 6,812,500 B2 | 11/2004 | Reeh et al. |
| 6,814,760 B2 | 11/2004 | Anderson et al. |
| 6,881,249 B2 | 4/2005 | Anderson et al. |
| 6,938,488 B2 | 9/2005 | Diaz et al. |
| 6,980,670 B1 | 12/2005 | Hoffman et al. |
| 7,066,908 B2 | 6/2006 | Kuracina et al. |
| 7,089,498 B1 | 8/2006 | Rathjen et al. |
| 7,145,330 B2 | 12/2006 | Xiao |
| 7,175,950 B2 | 2/2007 | Anderson et al. |
| 7,181,266 B2 | 2/2007 | Frangioni et al. |
| 7,215,687 B2 | 5/2007 | Kawai et al. |
| 7,235,189 B2 | 6/2007 | Höhn et al. |
| 7,285,364 B2 | 10/2007 | Anderson et al. |
| 7,344,587 B2 | 3/2008 | Khan et al. |
| 7,435,524 B2 | 10/2008 | Anderson et al. |
| 7,546,955 B2 | 6/2009 | Marty et al. |
| 7,549,960 B2 | 6/2009 | Govari |
| 7,558,616 B2 | 7/2009 | Govari et al. |
| 7,647,085 B2 | 1/2010 | Cane et al. |
| 7,651,505 B2 | 1/2010 | Lubock et al. |
| 7,791,593 B2 | 9/2010 | Cohen et al. |
| 7,869,011 B2 | 1/2011 | Christensen et al. |
| 7,910,022 B2 | 3/2011 | Agrawal et al. |
| 7,912,653 B1 | 3/2011 | Scher et al. |
| 7,917,298 B1 | 3/2011 | Scher et al. |
| 8,003,012 B2 | 8/2011 | Comanzo et al. |
| 8,177,792 B2 | 5/2012 | Lubock et al. |
| 8,442,281 B2 | 5/2013 | Jung et al. |
| 2001/0016696 A1 | 8/2001 | Bystrom et al. |
| 2002/0073099 A1 | 6/2002 | Gilbert et al. |
| 2002/0087437 A1 | 7/2002 | Hogan |
| 2002/0188470 A1 | 12/2002 | Hogan |
| 2003/0038721 A1 | 2/2003 | Hogan |
| 2003/0065294 A1 | 4/2003 | Pickup et al. |
| 2003/0113540 A1 | 6/2003 | Anderson et al. |
| 2003/0135128 A1 | 7/2003 | Suffin et al. |
| 2003/0159615 A1 | 8/2003 | Anderson et al. |
| 2003/0167964 A1 | 9/2003 | Anderson et al. |
| 2003/0176785 A1 | 9/2003 | Buckman et al. |
| 2004/0035208 A1 | 2/2004 | Diaz et al. |
| 2004/0122443 A1 | 6/2004 | Berryman et al. |
| 2004/0186773 A1 | 9/2004 | George et al. |
| 2004/0220527 A1 | 11/2004 | Buckley et al. |
| 2004/0236193 A1 | 11/2004 | Sharf |
| 2004/0253185 A1 | 12/2004 | Herweck et al. |
| 2004/0253281 A1 | 12/2004 | Herweck et al. |
| 2005/0061198 A1* | 3/2005 | Khan et al. ............. 106/31.03 |
| 2005/0100937 A1 | 5/2005 | Holmes |
| 2005/0160817 A1 | 7/2005 | Clement et al. |
| 2005/0172852 A1 | 8/2005 | Anderson et al. |
| 2005/0178287 A1 | 8/2005 | Anderson et al. |
| 2005/0208120 A1 | 9/2005 | Albani |
| 2005/0234336 A1 | 10/2005 | Beckman et al. |
| 2005/0251152 A1 | 11/2005 | Herweck et al. |
| 2006/0088355 A1 | 4/2006 | Ribi |
| 2006/0095061 A1 | 5/2006 | Trautman et al. |
| 2006/0108509 A1 | 5/2006 | Frangioni et al. |
| 2006/0173362 A1 | 8/2006 | Toms et al. |
| 2006/0228404 A1 | 10/2006 | Anderson et al. |
| 2007/0027429 A1 | 2/2007 | Kuracina et al. |
| 2007/0032846 A1 | 2/2007 | Ferren et al. |
| 2007/0106207 A1 | 5/2007 | Withey |
| 2007/0107625 A1 | 5/2007 | Anderson et al. |
| 2007/0116690 A1 | 5/2007 | Yang et al. |
| 2007/0162303 A1 | 7/2007 | Wiley, II et al. |
| 2007/0192195 A1 | 8/2007 | Asmar et al. |
| 2007/0224252 A1 | 9/2007 | Trautman et al. |
| 2008/0018429 A1 | 1/2008 | Kudoh et al. |
| 2008/0044746 A1 | 2/2008 | Anderson et al. |
| 2008/0125766 A1 | 5/2008 | Lubock et al. |
| 2008/0147038 A1 | 6/2008 | Hoffman |
| 2008/0161827 A1* | 7/2008 | Frost ....................... 606/116 |
| 2008/0177286 A1 | 7/2008 | Khan et al. |
| 2008/0208236 A1 | 8/2008 | Hobbs et al. |
| 2008/0247637 A1 | 10/2008 | Gildenberg |
| 2008/0257961 A1 | 10/2008 | Lubow |
| 2008/0269596 A1 | 10/2008 | Revie et al. |
| 2008/0287913 A1 | 11/2008 | Schwab |
| 2009/0018403 A1 | 1/2009 | Black et al. |
| 2009/0039158 A1 | 2/2009 | Grishin et al. |
| 2009/0076338 A1 | 3/2009 | Zdeblick et al. |
| 2009/0110730 A1 | 4/2009 | Fritz et al. |
| 2009/0131479 A1 | 5/2009 | Palmer et al. |
| 2009/0210165 A1 | 8/2009 | Christensen et al. |
| 2010/0125028 A1 | 5/2010 | Heppert |
| 2010/0163623 A1 | 7/2010 | Mays et al. |
| 2010/0211079 A1 | 8/2010 | Aramant |
| 2010/0217065 A1 | 8/2010 | Khan et al. |
| 2010/0221188 A1 | 9/2010 | Clark et al. |
| 2011/0148984 A1 | 6/2011 | Ribi |
| 2011/0237860 A1 | 9/2011 | Khan et al. |
| 2011/0275930 A1 | 11/2011 | Jho et al. |
| 2011/0313288 A1 | 12/2011 | Chi Sing et al. |
| 2012/0150023 A1 | 6/2012 | Kaspar et al. |
| 2012/0203572 A1 | 8/2012 | Christensen |
| 2012/0215230 A1 | 8/2012 | Lubock et al. |
| 2012/0238906 A1 | 9/2012 | Gilchrest et al. |
| 2012/0283637 A1 | 11/2012 | Cohen |

(56) References Cited

U.S. PATENT DOCUMENTS

2013/0046182 A1 2/2013 Hegg et al.
2013/0197447 A1 8/2013 Smith

OTHER PUBLICATIONS

Birdwell, Robyn L. et al., "Clip or Marker Migration 5-10 Weeks after Stereotactic 11-gauge Vacuum-assisted Breast Biopsy: Report of Two Cases[1]" Radiology, Nov. 2003, pp. 541-544, RSNA.
"Contrast Resolution", Wikipedia, located at http://en.wikipedia.org/wiki/Contrast_resolution, printed on Jun. 28, 2012, pp. 1-2.
Couture, O. et al., "Model for the ultrasound reflection from micro-beads and cells distributed in layers on a uniform surface", Phys Med Biol., Jul. 21, 2007, pp. 1-1, vol. 52, No. 14. (Abstract Only).
"Encoded microparticles for isolated cell and embryo tracking", located at http://www.uab.es/servlet/Satellite/serveis-a-empreses/oferta-tecnologica-1245651215252.html?param1=3021, printed on Jul. 27, 2012, Parc de Recerca UAB.
Gattiker, F. et al., "Novel ultrasound read-out for a wireless implantable passive strain sensor (WIPSS)", Sensors and Actuators, 2008, pp. 291-298, vol. A 145-146, Elsevier B.V.
Ho, Yi-Ping et al., "Multiplexed Hybridization Detection with Multicolor Colocalization of Quantum Dot Nanoprobes", Nano Letters, 2005, pp. 1693-1697, vol. 5, No. 9, American Chemical Society.
"Markers for predictable placement and rapid expansion", Mammotome, located at http://www.mammotome.com/Mammotome/Products/Tissue-Markers/index.htm, printed on Aug. 30, 2012, pp. 1-2, Devicor Medical Products, Inc.
Murray, Charles J., "Injectable Chip Opens the Door to 'Human Bar Code'", EETimes.com, located at http://resnse.com/general18/injectable.htm, printed on Jul. 27, 2012, pp. 1-6.
Serago, Christopher F. et al., "Comparison of Daily Megavoltage Electronic Portal Imaging or Kilovoltage Imaging with Marker Seeds to Ultrasound Imaging or Skin Marks for Prostate Localization and Treatment Positioning in Patients with Prostate Cancer", Int. J. Radiation Oncology Biol. Phys, 2006, pp. 1585-1592, vol. 65, No. 5, Elsevier Inc.
Stern, Roger A. et al., "A Biologically Compatible Implantable Ultrasonic Marker", Ultrasound in Medicine & Biology, 1983, pp. 191-199, vol. 9, No. 2, Pergamon Press Ltd.
Stoll, Jeffrey et al., "Passive Markers for Ultrasound Tracking of Surgical Instruments", MICCAI 2005, LNCS 3750, 2005, pp. 41-48, Springer-Verlag Berlin Heidelberg.
"Tissue Markers"; Mammotome, a division of Devicor Medical Products, Inc.; 2 pages; May 17, 2011; located at https://web.archive.org/web/20110517031051/http://www.mammotome.com/Mammotome/Products/Tissue-Markers.
Tomasi, Carlo, "Computer Vision", CPS 274 Lecture Notes—Duke University, Fall 2009.
"UltraClip® Dual Trigger Breast Tissue Marker", located at http://www.bardbiopsy.com/products/ultraclip_dual.php, printed on Aug. 20, 2012, C. R. Bard, Inc.
Baldo et al.; "Highly efficient phosphorescent emission from organic electroluminescent devices"; Nature; Sep. 10, 1998; pp. 151-154; vol. 395; Macmillan Publishers Ltd.
Borisov et al.; "Phosphorescent Platinum(II) and Palladium(II) Complexes with Azatetrabenzoporphyrins—New Red Laser Diode-Compatible Indicators for Optical Oxygen Sensing"; ACS Applied Materials & Interfaces; Published on Web Feb. 2, 2010; pp. 366-374; vol. 2, No. 2; American Chemical Society.
Botchway et al.; "Time-resolved and two-photon emission imaging microscopy of live cells with inert platinum complexes"; PNAS; Oct. 21, 2008; pp. 16071-16076; vol. 105, No. 42; The National Academy of Sciences of the USA.
Chou et al.; "Phosphorescent dyes for organic light-emitting diodes"; Chemistry; 2007; pp. 380-395; vol. 13, No. 2; 2 pages of book overview printed on Apr. 4, 2012.
De Haard et al.; "A Large Non-immunized Human Fab Fragment Phage Library That Permits Rapid Isolation and Kinetic Analysis of High Affinity Antibodies"; The Journal of Biological Chemistry; Jun. 25, 1999; pp. 18218-18230; vol. 274, No. 26; The American Society for Biochemistry and Molecular Biology, Inc.
Dubach et al.; "In vivo sodium concentration continuously monitored with fluorescent sensors"; Integr Biol; Feb. 2011; pp. 142-148; No. 3, No. 2; (Abstract, only one page).
Filonov et al.; "Bright and stable near-infrared fluorescent protein for in vivo imaging"; Nature Biotechnology; Aug. 2011; pp. 757-763; vol. 29; Nature America, Inc.
Han et al.; "Quantum-dot-tagged microbeads for multiplexed optical coding of biomolecules"; Nature Biotechnology; Jul. 2001; pp. 631-635; vol. 19; Nature Publishing Group.
Holland et al.; "Intradermal influenza vaccine administered using a new microinjection system produces superior immunogenicity in elderly adults: a randomized controlled trial"; J Infect Dis; Sep. 1, 2008; pp. 650-658; vol. 198, No. 5; Infectious Disease Society of America.
Keck et al.; "Aripiprazole Monotherapy for Maintenance Therapy in Bipolar I Disorder: A 100-Week, Double Blind Study Versus Placebo"; J. Clin. Psychiatry; Oct. 2007; pp. 1480-1491; vol. 68, No. 10.
Kim et al.; "Polymer encapsulation of yttrium oxysulfide phosphorescent particles via miniemulsion polymerization"; Journal of Polymer Science Part A: Polymer Chemistry; Mar. 15, 2007; pp. 1038-1054; vol. 45, Issue No. 6; (abstract only) three pages printed on May 7, 2012 from onlinelibrary.wiley.com/doi/10.1002/pola.21860/abstract.
Kumar et al.; "Near-Infrared Phosphorescent Polymeric Nanomicelles: Efficient Optical Probes for Tumor Imaging and Detection"; ACS Appl. Mater. Interfaces; Published on Web Jun. 22, 2009; pp. 1474-1481; vol. 1, No. 7; American Chemical Society.
Kumar et al.; "Supporting Information NIR phosphorescent polymeric nanomicelles: efficient optical probes for tumor imaging and detection"; 7 pgs.; printed on May 4, 2012.
Larson et al.; "Water-Soluble Quantum Dots for Multiphoton Fluorescence Imaging in Vivo"; Science; May 30, 2003; pp. 1434-1436; vol. 300, No. 5624.
Lee et al.; "Artificially engineered magnetic nanoparticles for ultra-sensitive molecular imaging"; Nature Medicine; Jan. 2007; pp. 95-99; vol. 13, No. 1; Nature Publishing Group.
Lee et al.; "Dissolving Microneedles for Transdermal Drug Delivery"; Biomaterials; May 2008; pp. 2113-2124; vol. 29, No. 13.
Madhwal et al.; "Self-trapping mechanism in green phosphorescent dye-doped polymer light-emitting diodes"; Physica Scripta; bearing a date of 2010; vol. 81, No. 6; (abstract; 2 pgs.); printed on Apr. 4, 2012.
McAllister et al.; "Microfabricated needles for transdermal delivery of macromolecules and nanoparticles: Fabrication methods and transport studies"; PNAS; Nov. 25, 2003; pp. 13755-13760; vol. 100, No. 24; The National Academy of Sciences of the USA.
Mendioroz et al.; "Infrared to visible and ultraviolet upconversion processes in $Nd^{3+}$-doped potassium lead chloride crystal"; Optical Materials; Sep. 2004; pp. 351-357 (four pages printed from vol. 26, Issue No. 4).
M-M-R® II (Measles, Mumps, and Rubella Virus Vaccine Live); Product Information Sheet; Dec. 2010; pp. 1-12; Merck Sharp & Dohme Corp. a subsidiary of Merck & Co., Inc.
Park et al.; "Biodegradable Polymers for Microencapsulation of Drugs"; Molecules; 2005; pp. 146-161; vol. 10; located at www.mdpi.org.
"Phosphorescent Nanoparticles"; Active Motif Chromeon; bearing a date of 2012; three pages; printed on Apr. 4, 2012; Active Motif Chromeon GmbH.
Price et al.; "Engineered cell surface expression of membrane immunoglobulin as a means to identify monoclonal antibody-secreting hybridomas" Journal of Immunological Methods; bearing a date of 2009; pp. 28-41, No. 343; Elsevier B.V.
"QE65000-FL Scientific-grade Spectrometer"; Ocean Optics; product information; 3 pgs.; printed on May 7, 2012; located at www.oceanoptics.com/products/qe65000FL.asp.

(56) References Cited

OTHER PUBLICATIONS

Saber et al.; "Partial shape recognition by sub-matrix matching for partial matching guided image labeling"; Pattern Recognition; bearing a date of 2005; pp. 1560-1573; vol. 38; Elsevier Ltd.
Schneider et al.; "A One-step Purification of Membrane Proteins Using a High Efficiency Immunomatrix" The Journal of Biological Chemistry; Sep. 25, 1982; pp. 10766-10769; vol. 257, No. 18.
Shibita et al.; "Injectable hydrogel microbeads for fluorescence-based in vivo continuous glucose monitoring"; PNAS; Oct. 19, 2010; pp. 17894-17898; vol. 107, No. 42.
Song et al.; "Bright and Mon dispersed Phosphorescent Particles and Their Applications for Biological Assays"; Anal. Chem.; Jul. 15, 2008; pp. 5501-5507; vol. 80, No. 14; American Chemical Society.
Yeo et al.; "Control of Encapsulation Efficiency and Initial Burst in Polymeric Microparticle Systems"; Arch Pharm Res; 2004; pp. 1-12; vol. 27, No. 1.
Zimmermann et al.; Electro manipulation of Mammalian Cells: Fundamentals and Application; IEEE Transactions on Plasma Science; Feb. 2000; pp. 72-82; vol. 28, No. 1; IEEE.

\* cited by examiner

DEVICES AND METHODS FOR RECORDING INFORMATION ON A SUBJECT'S BODY

RELATED APPLICATIONS

For purposes of the USPTO extra-statutory requirements, the present application constitutes a continuation-in-part of U.S. patent application Ser. No. 13/199,038, entitled DEVICES AND METHODS FOR RECORDING INFORMATION ON A SUBJECT'S BODY, naming Roderick A. Hyde, Jordin T. Kare, Wayne R. Kindsvogel, Royce A. Levien, Erez Lieberman, Mark A. Malamud, Nathan P. Myhrvold, Elizabeth A. Sweeney, Clarence T. Tegreene, Charles Whitmer and Lowell L. Wood, Jr. as inventors, filed 16 Aug. 2011, now abandoned, which is currently an application of which a currently co-pending application is entitled to the benefit of the filing date.

For purposes of the USPTO extra-statutory requirements, the present application constitutes a continuation-in-part of U.S. patent application Ser. No. 13/199,046, entitled DEVICES AND METHODS FOR RECORDING INFORMATION ON A SUBJECT'S BODY, naming Roderick A. Hyde, Jordin T. Kare, Wayne R. Kindsvogel, Royce A. Levien, Erez Lieberman, Mark A. Malamud, Nathan P. Myhrvold, Elizabeth A. Sweeney, Clarence T. Tegreene, Charles Whitmer and Lowell L. Wood, Jr. as inventors, filed 16 Aug. 2011, now U.S. Pat. No. 9,443,061, which is currently an application of which a currently co-pending application is entitled to the benefit of the filing date.

For purposes of the USPTO extra-statutory requirements, the present application constitutes a continuation-in-part of U.S. patent application Ser. No. 13/199,047, entitled DEVICES AND METHODS FOR RECORDING INFORMATION ON A SUBJECT'S BODY, naming Roderick A. Hyde, Jordin T. Kare, Wayne R. Kindsvogel, Royce A. Levien, Erez Lieberman, Mark A. Malamud, Nathan P. Myhrvold, Elizabeth A. Sweeney, Clarence T. Tegreene, Charles Whitmer and Lowell L. Wood, Jr. as inventors, filed 16 Aug. 2011, now U.S. Pat. No. 9,286,615 which is currently an application of which a currently co-pending application is entitled to the benefit of the filing date.

For purposes of the USPTO extra-statutory requirements, the present application constitutes a continuation-in-part of U.S. patent application Ser. No. 13/474,995, entitled DEVICES AND METHODS FOR RECORDING INFORMATION ON A SUBJECT'S BODY, naming Michael C. Hegg, Roderick A. Hyde and Jordin T. Kare as inventors, filed 18 May 2012, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation, continuation-in-part, or divisional of a parent application. Stephen G. Kunin, Benefit of Prior-Filed Application, USPTO Official Gazette Mar. 18, 2003. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant has provided designation(s) of a relationship between the present application and its parent application(s) as set forth above, but expressly points out that such designation(s) are not to be construed in any way as any type of commentary and/or admission as to whether or not the present application contains any new matter in addition to the matter of its parent application(s).

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)). All subject matter of the Related Applications and of any and all parent, grandparent, great-grandparent, etc. applications of the Related Applications, including any priority claims, is incorporated herein by reference to the extent such subject matter is not inconsistent herewith.

SUMMARY

Various embodiments are disclosed herein that relate to methods, devices, systems, and computer program products for providing at least one information mark to a subject in conjunction with administration of at least one medical treatment to the subject. In an embodiment, the at least one information mark represents information regarding the at least one medical treatment, and optionally entitlement of the recipient subject to at least one reward based on the administration of the at least one medical treatment. In an embodiment, a method includes providing at least one information mark to a subject in conjunction with administration of at least one therapeutic agent to the subject. In an embodiment, the at least one information mark represents information regarding the at least one therapeutic agent, and entitlement of the recipient subject to at least one reward based on the administration of the at least one therapeutic agent. In an embodiment, a method provides at least one reward for receipt by a subject of a medical treatment, including monitoring the subject for administration of a medical treatment by the subject or another entity, generating information relating to the medical treatment of the subject, transmitting at least some information relating to the medical treatment; and providing an entitlement to the recipient subject of at least one reward. In an embodiment, the at least one information mark includes one or more spatial coding. In an embodiment, the at least one information mark includes one or more spectral coding.

In an embodiment, devices, computer systems, computer program products, and computer-implemented methods assist or provide for administration of at least one information mark to a subject in conjunction with administration of at least one medical treatment.

In an embodiment, devices, computer systems, computer program products, and computer-implemented methods assist or provide for administration of at least one information mark to a subject that includes one or more magnetic particles.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
FIG. 1 illustrates a partial view of a particular embodiment described herein.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

In an embodiment, at least one of the methods, devices, or computer systems disclosed herein are utilized for documenting information regarding a subject's health, including but not limited to vaccination history, or health status. In an embodiment, a device (e.g., an injector) is configured to administer an information mark (e.g., including information relating to administration of at least one medical treatment (including medical intervention such as diagnosis, prognosis, prevention, etc.), including but not limited to administration of at least one therapeutic agent (e.g., vaccination or other agent); information relating to prescribed therapeutic agents; information relating to passwords for the subject's implantable medical devices or other related medical devices; information relating to a subject's weight or height; information relating to a subject's medical history including allergies, genetic predisposition(s) to particular diseases or disorders, mental health history or behavioral tendencies, use of alcohol, tobacco, or other drugs, number of offspring, pregnancies, fertility or ovulation cycle; information relating to a subject's history of drug treatment or mental health treatment; information relating to a subject's insurance carrier or other third party payor; or other information on a subject in a visible or non-visible manner. In an embodiment, the information mark includes at least one piece of information that is unique to the subject to whom it is administered. That is, in certain aspects, the information marks are able to be customized to the subject who is receiving the particular medical treatment. Information relating to administration of a therapeutic agent includes, but is not limited to, the type of therapeutic agent, dosage, date, administrator, manufacturer, lot, location site of clinic, medical history, allergies, laboratory test results, next suggested dose, etc. In an embodiment, at least one information mark relates to a future administration of a medical treatment (e.g., surgery).

In an embodiment, a subject includes, but is not limited to, a human or non-human animal (for example, pet, livestock, food animals, wild animals, game animals, etc.).

In an embodiment, the information is provided by a magnetic, reflective, fluorescent, acoustic-scattering (e.g., ultrasonic scattering), luminescent, radioactive, conductive, or other marker that provides a measurable characteristic for "reading" the information contained within the information mark or is represented by the information mark (e.g., by emitting one or more signals, or by providing non-emitting data). In an embodiment, at least one parcel of information relating to the information mark is coded or encrypted. In an embodiment, the information mark includes information that can interact with or be linked to an electronic personal health record. Some non-limiting examples of magnetic ink are disclosed in U.S. Pat. No. 7,344,587, which is incorporated herein by reference.

In an embodiment, the fluorescent marker includes, but is not limited by, phytochrome-based near-infrared fluorescent protein (iRFP), as described for example, in *Nature Biotech.*, Vol. 29, No. 8, pp. 757-761, which is incorporated herein by reference.

In an embodiment, the information mark can be further manipulated (e.g., "erased," encoded, re-coded, etc.). In an embodiment, the information mark can expire or become "unreadable" after a given time period. In an embodiment, the information mark can be set to not be "readable" immediately, but emit a signal once a time period has passed (e.g., to alert of the need for further dosing of a therapeutic agent). For example, in an embodiment, a given time period includes at least about one hour, at least about two hours, at least about three hours, at least about four hours, at least about five hours, at least about a day, at least about two days, at least about three days, at least about four days, at least about five days, at least about one week, at least about two weeks, at least about three weeks, at least about four weeks, at least about five weeks, at least about one month, or more.

In an embodiment, the information mark includes a marking visible or invisible to the naked eye. In an embodiment, the information mark can be "read" via reflection at specific wavelength(s) (e.g., infrared, visible, ultraviolet, etc.). In an embodiment, the information mark can be "read" via fluorescence (e.g., quantum dots). In an embodiment, the information mark is magnetic or conductive and is "readable" by electronic or magnetic devices. In an embodiment, the information mark is administered to a subject with the subject's knowledge. In an embodiment, the information mark is administered to a subject without the subject's knowledge. In an embodiment, the device configured to administer the information mark to a subject includes at least one of a needle, inhaler, transdermal patch, microneedle, needle array, inkjet, needle-less injection (including but not limited to microprotrusions, microneedles, cannula, microcannula, polymer microneedles), etc. In an embodiment, needle-less injection can include metal, biodegradable, hollow, solid, etc. and other formations or formulations. For example, hollow protrusions can include a trough, which provides capillary motion and coating via this capillary motion or jet propulsion. See for example, U.S. Pat. App. Pub. No. 2007/0224252, which is incorporated herein by reference. In an embodiment, a needle leaves a hidden notation designating it was used (e.g., dispensing of X-Ray Fluorescent-readable material).

In an embodiment, the at least one information mark indicates a specific medical treatment (e.g., chemotherapy, stem cell transplant, etc.) has been administered to a subject.

In an embodiment, the at least one information mark includes at least one of magnetic ink, RFID ink (e.g., Somark's), LED, silk silicon implant, or quantum dot(s).

In an embodiment, a receiver is configured for receiving an information signal from the information mark. In an embodiment, the receiver optionally forwards at least some of the information from the information mark to a database (e.g., computer system), where the information can be stored (e.g., in a database). In an embodiment, the computer system including the database also includes one or more input/output devices to provide for entry of inputs by a user or for the presentation of information to the user. Various types of input/output devices are known, including for example, audio, visual, electronic, tactile, or other forms (e.g., scanner, touchscreen, keyboard, mouse, trackball, button, dial, microphone, speaker, video display, etc.). In an embodiment, the computer system includes a controller, which can be one or more of hardware, software, or firmware. In an embodiment, the controller includes a microprocessor. In an embodiment, the computer system includes an imaging device (e.g., CCD camera, or sensor system, etc.).

In an embodiment, a comparator (e.g., as part of the computer system), is configured to compare at least two parcels of information relating to the subject. For example, the comparator can be configured to compare a type, quantity, or timing of a therapeutic agent received by the subject (e.g., vaccination), with the type, quantity, or timing of the therapeutic agent prescribed by a physician or other health care provider. For example, comparator software modules are known. See, for example, U.S. Patent Pub. No. 2002/0087437, which is incorporated herein by reference.

In an example, the comparator can be configured to compare a type, quantity, or timing of a therapeutic agent prescribed by the subject with a type, quantity, or timing of a therapeutic agent available at the healthcare facility or in a pharmacy warehouse. In another example, the comparator can be configured to compare a type, quantity, or timing of a therapeutic agent taken at present by the subject, or taken in the past (e.g., by linking with the subject's electronic health record). In another example, the comparator can be configured to compare a type, quantity, or timing of a therapeutic agent prescribed for the subject, with any known allergies of the subject (e.g., by linking with the subject's electronic health record).

In an embodiment, an information signal from the information mark is automatically linked to an electronic health record, or automatically creates an electronic health record, and is optionally automatically entered into a database of other information about the subject or (an)other subject(s). For example, in an embodiment, an electronic health record includes a population database. In an embodiment, the population database includes information submitted anonymously. In an embodiment, the population database includes information submitted with identifying information such that an individual subject is identifiable. In an embodiment, the population database includes at least some information submitted anonymously and at least some information submitted with identifying information. In an embodiment, the population database includes at least one protocol or computer algorithm to avoid submission of the same information twice.

In an embodiment, the device configured to administer the information mark is also capable of "reading" the same and/or other information marks. In an embodiment, the information mark is read by the subject itself. In an embodiment, the information mark is read by a second or third party. In an embodiment, the information mark is read by another party in order to ensure compliance, reward, insurance coverage, public health assessment, or other instances.

In an embodiment, upon receiving an information mark, the subject is entitled to at least one reward. The reward can include, but is not limited to, for example, monetary rewards, or discounted or free products or services. In an embodiment, the subject receives an information mark including information relating to entitlement of at least one reward. In an embodiment, receipt of several information marks enable the subject to be eligible for increasingly beneficial rewards (for example, each additional mark increases the discount on the product or service until enough information marks have been administered to earn the subject a free product or service). In an embodiment, at least one reward includes a "credit" with a health insurance company, or third party medical expense payor. In an embodiment, the subject is included in a cohort of other subjects—some of which are receiving a therapeutic agent (e.g., vaccination), and some of which are not (e.g., refusal of vaccination or non-compliance with medical prescriptions, etc.) and those subjects that are receiving a therapeutic agent receive information marks that entitle them to at least one reward, while the subjects that are not receiving a therapeutic agent do not receive the information mark, and are not entitled to the same reward.

In an embodiment, an information mark allows the subject a selection of possible rewards. In an embodiment, receipt of multiple information marks allows the subject a broader selection of possible rewards. In an embodiment, receipt of multiple information marks allows the subject a greater selection of higher value rewards (e.g., more valuable products or services, or greater discount on a product or service). In an embodiment, one or more information marks from one subject include information that is electronically linked to one or more information marks from at least one other subject.

For example, a first family member receives a vaccination, and a corresponding information mark. A second family member receives a vaccination, and at least some of the information from his or her information mark is electronically linked to the first family member's information mark in an electronic registry (e.g., a computer database) for purposes of identification, convenience, third party payor purposes, etc., and can optionally enable the first and second family members to receive entitlement to higher value rewards due to compliance of multiple family members. In an embodiment, at least some of the information of at least one information mark is capable of being electronically linked to an electronic health record. Such an electronic health record can be shared with, for example, other family members, or a third party payor. In an embodiment, electronically linking the information from an information mark to an electronic health record enables the subject to receive entitlement to a higher value reward, or a greater selection of rewards.

In an embodiment, a method for rewarding receipt by a subject of a medical treatment (e.g., receiving at least one therapeutic agent) includes at least one of monitoring the subject for administration by the subject or another individual, of a medical treatment to the subject, generating information relating to the medical treatment of the subject, transmitting or transferring at least some information relating to the medical treatment (e.g., administration of at least one therapeutic agent) to a subject by way of a computing system (e.g., computer, internet, processor, etc.), and optionally converting at least some of the information relating to the medical treatment into reward points for the subject. In an embodiment, the receipt by the subject of a medical treatment is monitored, and information relating to entitlement of reward for the subject is based on successful receipt of a medical treatment.

In an embodiment, the computing system includes, for example, at least one of a notebook computer, a personal data device, a desktop computer, a cluster of processors, a cluster of servers, a cloud computing center, a mobile telephone, or other computing device.

In an embodiment, a computer or other processing unit is configured to receive or transmit information relating to receipt of a therapeutic agent by a subject by, for example, a USB cable or wireless network. In an embodiment, a computer or other processing unit is configured for receiving or storing information. In an embodiment, a computer or other processing unit is configured to allocate or regulate establishment or usage of reward points, or reward redemption. See, for example, U.S. Pat. No. 6,980,670, which is incorporated herein by reference.

In an embodiment, the computer or other processing unit is configured to allow input of additional reward points, or information relating to administration of a medical treatment (e.g., therapeutic agent), for example, as in an account. In an embodiment, the account is an individual account. In an embodiment, the account is a group account. In an embodiment, an administrator or other participating subject can input information or reward points into a particular account based on receipt of a therapeutic agent by the subject. In an embodiment, a computer or other processing unit displays at least some information relating to receipt of a therapeutic agent to a subject. In an embodiment, at least some information relating to receipt of a medical treatment (e.g., therapeutic agent) by a subject is graphically displayed to an entity (e.g., human or computer). See, for example, U.S. Patent App. Pub. No. 2010/0125028, which is incorporated herein by reference.

In an embodiment, at least one information mark is readable by a device (e.g., handheld wand, portable device, wall mounted unit, doorway detector, etc.) at a hospital, clinic, other healthcare facility, or other public institution (school, airport, library, etc.). In an embodiment, if the subject passes by an information mark reader, the subject can have the option of receiving a medical treatment (e.g., therapeutic agent) at that time (e.g., vaccine "booster," or other therapeutic agent). In an embodiment, the subject can be required to receive a medical treatment (e.g. therapeutic agent) in order to proceed (exit the building or other space, continue to enter the building or other space (e.g., library, school, airport, etc.)), such as, for example, during a state of emergency or public health threat.

For example, the information mark reader can include, but is not limited to, a cell phone device, other handheld device, other portable device, a device built into a structure (for example, as part of a vehicle or doorway, etc.). In an embodiment, the information mark reader includes a camera, for example a camera/LED/filter as described in U.S. Patent App. Pub. No. 2010/0221188, and Dubach et al., Integr. Biol. 3, Abstract, pp. 142-148 (2011); each of which is incorporated herein by reference.

In an embodiment, a comparator is configured to compare at least two parcels of information from a subject's information mark(s) with each other, or compare at least one parcel of information from a subject's information mark to at least one parcel of information in an electronic registry (e.g., database). In an embodiment, a comparator is configured to determine if additional medical treatment is warranted. In an embodiment, a comparator is configured to determine what additional medical treatment is warranted.

In an embodiment, at least one information mark indicates the subject has health information stored in one or more electronic registry (e.g., electronic health records). In an embodiment, at least some of the information from one or more information marks is electronically linked to at least some other information from one or more electronic health record. In an embodiment, at least one information mark represents information related to health history, as described herein, one or more links to information or data files. In an embodiment, at least some of the information in an information mark is encrypted. In an embodiment, the information mark includes timing information (e.g., for past administration of a pharmaceutical drug, or predicted administration or need of a pharmaceutical drug).

In an embodiment, a device (optionally linked to a computer system, including but not limited to a personal computer or personal data device) is configured to receive (and optionally interpret) at least some of the information included in the at least one information mark of the subject. In an embodiment, the device is further configured to gather or receive at least some information from an electronic health record. In an embodiment, a device or computer system configured to receive (and optionally interpret, or "read" the information contained in the information mark) at least some of the information represented by the at least one information mark of the subject, further is configured to make a determination (e.g., course of treatment, vaccine selection, dosage of therapeutic agent, potential allergy or drug interaction or incompatibility, etc.) based on at least some of the information of the subject's electronic health record. In an embodiment, the device configured to receive at least some of the information of the information mark is further configured to transmit at least some of the information to an electronic registry (e.g., database or electronic record).

In an embodiment, the information mark is human or non-human readable. In an embodiment, the information mark includes at least one representation (e.g., shape, animal, number, letter, or other symbol) that signifies at least one parcel of information, or single fact relating to the subject or subject's treatment. In an embodiment, the material(s) utilized to construct the information mark include, for example quantum dots, luminex dots, etc.

For example, non-human readable information marks include information marks that are machine readable, and can be in a form, for example, that can be read, captured, scanned, sensed, or imaged by a machine (e.g., computer), and optionally interpreted by the machine's hardware or software system. Non-limiting examples of information marks including non-human readable components include one-, two-, or multi-dimensional symbologies, stacked symbologies, fixed-length symbologies, multiple-width symbologies, variable-length symbologies, discrete symbologies, continuous symbologies, etc. Some specific examples include, but are not limited to: APOSTAL, CODE 128, CODE 39, CODE 49, CODE 93, CODE 931, CODE ONE, CODEABAR, DATA MATRIX, MAXICODE, PDF417, CODABAR, CODE 25, CODE 39, FULLASCII, CODE 39 HIBC, CODE 11, EAN-13, EAN-8, EAN supplements, ISBN/BOOKLAND, ITF25, MSI/PLESSEY, POSTNET, UCC/EAN-128, UPC/EAN, UPC-A, UPC-E, UPC supplements, and the like. Further discussion and examples of non-human readable symbols can be found, for example, in U.S. Pat. No. 7,546,955, which is incorporated herein by reference.

In other examples, human readable information marks can include, for example, alphabets (e.g., English, Japanese, Cyrillic, Greek, Hebrew, Chinese, Kanji, Arabic, Farsi, French, German, Latin, Italian, Spanish, etc.). Other examples of human readable information mark symbols include, but are not limited by, optical character recognition fonts, OCR-A, OCR-B, OCRA I, OCRA III, OCRA IV, OCRB I, OCRB III, and OCRB IV, etc. Other specific non-limiting examples can be found, for example, in U.S. Pat. No. 7,546,955, Ibid.

In an embodiment, as can be seen in the Figures, the at least one information mark and the at least one therapeutic agent have different spatial locations on the subject's body. In an embodiment, the at least one information mark and the at least one therapeutic agent have different temporal locations on the subject's body. In an embodiment, the subject includes at least one animal. In an embodiment, the subject includes at least one plant. In an embodiment, the subject is a mammal, reptile, amphibian, fish, or bird. In an embodiment, the subject is a human. In an embodiment, the subject is a domesticated animal, including but not limited to a horse, cow, dog, cat, sheep, pig, or other animal. In an embodiment, an information mark is deposited on or in the subject's skin (e.g., dermis, epidermis, etc.). In an embodiment, an information mark is deposited on or in another tissue of the subject (e.g., scalp, oral cavity, eyelid, ear canal, nasal passage, or other soft tissue location). In an embodiment, an information mark is deposited in a fatty part of the subject's body (e.g., arm, leg, belly, etc.). In an embodiment, an information mark is deposited in a thick-skinned area of the subject (e.g., sole of the foot, skin of the back, etc.). In an embodiment, an information mark is deposited on the ear of the subject. In an embodiment, an information mark is deposited between the shoulder blades of the subject.

In an embodiment, the material(s) utilized to construct the information mark include a spatial or temporal pattern or other representation that signifies certain information. For example, measuring certain biometric characteristics of a subject can be utilized as unique identifiers (e.g., fingerprints, iris scan, retinal scan, etc.). For example, computer algorithms have been developed for ease of measuring points and patterns of such biometric characteristics. See, for example, "Singular Point Detection in Fingerprints Using Quadrant Change Information," Kryszczuk and Drygaijlo, on the world wide web at: portal.acm.org/citation.cfm?id=1172857, last visited on Jun. 8, 2011, the content of which is incorporated herein by reference. Furthermore, partial shape recognition algorithms have been developed that are translation, rotation, scale, and reflection invariant. See, for example, "Partial Shape Recognition by Sub-matrix Matching for Partial Matching Guided Image Labeling," Saber, et al., Pattern Recogn., pp. 1560-1573 (2005).

Thus, in an embodiment, by determining one or more specific spatial or temporal pattern(s) desired, a pre-determined spatial or temporal pattern is designed as a unique identifier for a particular subject, corresponding to at least one unique attribute of that subject including but not limited to height, weight, genomic or proteomic profile, genetic information, social security number, random assigned identifier, familial relationship(s), medical treatment, receipt of at least one therapeutic agent, predicted medical treatment, or other identifier. For example, as a temporal pattern is constructed over time (e.g., receiving multiple vaccinations of the same or different type), each step of constructing the pattern, or the completed pattern, or various stages of completion can entitle the subject to one or more rewards. In an embodiment, as the pattern is constructed, the value or frequency of the reward is increased. In an embodiment, multiple layers of complexity are built into the pattern, so that a first portion completed is able to trigger a special reward once a second portion is completed. In an embodiment, completion of at least one portion allows the subject to move on to a second level of complexity of the pattern, and begin to complete a second portion of the pattern. In an embodiment, a device is configured to read multiple information marks, optionally including spatial or temporal patterns.

In an embodiment, at least some of the information included in the spatial or temporal pattern is electronically linked to an electronic registry (e.g., electronic health record). In an embodiment, the electronic health record is only for the subject receiving the medical treatment. In an embodiment, the electronic health record includes at least part of a cohort of subjects.

In an embodiment, at least one information mark is included in a therapeutic agent (e.g., in solution, in suspension, in simultaneous administration delivery mechanism, etc.), such that the information mark is administered to the subject simultaneously with the therapeutic agent.

In an embodiment, a device configured for administering the at least one information mark, or for "reading" an information mark, is further configured for accessing information from one or more electronic sources (e.g., world wide web, database, etc.) and incorporating it into the information mark, or interpreting the information mark in light of the accessed information. For example, the device can include a transmitter, transceiver, receiver, or other component that is configured to send or receive information from one or more electronic sources.

In an embodiment, a system includes collecting and optionally maintaining data in a database regarding medication compliance (e.g., computer and optional computer network). In an embodiment, the system collects at least some information from a detector or reader set up in a public area, for example a public walkway (e.g., airport, school, etc.) or a public waiting area or a public vehicle (e.g., an airplane, train, or bus). In an embodiment, the subject is unaware that his or her information mark(s) have been scanned or read.

In an embodiment, authorization to access or read an information mark on a subject is provided for various entities (e.g., school administrators, law enforcement officials, health care providers, public health officials, the military, etc.), and each entity can access information included in an information mark of a subject according to that particular entity's authorization level. In an embodiment, a device or computer system described herein further comprises means for collecting personal information relating to the subject that is not included in the at least one information mark. For example, the means for collecting personal information includes, but is not limited to, circuitry configured for collecting personal information. In an embodiment, a method includes collecting personal information relating to the subject that is not included in the at least one information mark.

In an embodiment, a device or computer system described herein further comprises means for comparing information included in the at least one information mark with the personal information collected. For example, the means for comparing information includes, but is not limited to, circuitry configured for comparing information. In an embodiment, a method includes comparing information included in the at least one information mark with the personal information collected.

In an embodiment, a device or computer system described further comprises means for transmitting the personal information relating to the subject to at least one electronic registry. In an embodiment, means for transmitting the personal information relating to the subject to at least one electronic registry includes, but is not limited to, circuitry configured for transmitting the personal information relating to the subject to at least one electronic registry. In an embodiment, the computer system or device includes a wireless transmitter. In an embodiment, the computer system or device includes a wired transmitter. In an embodiment, a method described herein further comprises transmitting the personal information relating to the subject to at least one electronic registry.

In an embodiment, a computer system or device described herein further comprises means for selecting authorization to access or read information included in the at least one information mark of the subject. In an embodiment, the means for selecting authorization to access or read information included in the at least one information mark of the subject includes, but is not limited to, circuitry configured for selecting authorization to access or read information included in the at least one information mark of the subject. In an embodiment, a method described herein further comprises selecting authorization to access or read information included in the at least one information mark of the subject.

In an embodiment, any method described herein is a computer-implemented method.

In an embodiment, a database that records, compares, or otherwise is linked to, interacts with, or is utilized with an information mark is configured to be queried, searched, allow for comparison or analysis of data, allow for filtering, sorting, editing, or otherwise manipulating by a user. In an embodiment, the user is a human. In an embodiment, the user is a computer or computer system (including a software module, for example).

In an embodiment, a first electronic registry (including but not limited to an electronic health record) is created. In an embodiment, the first electronic registry includes, but is not limited to, personal health information. In an embodiment, a second electronic registry (as part of the first electronic registry, or separate therefrom) is created. In an embodiment, the second electronic registry includes, but is not limited to, a reward provider's products or services. In an embodiment, a third electronic registry (as part of the first or second electronic registries, or separate therefrom either or both) is created. In an embodiment, the third electronic registry includes, but is not limited to, the subject's reward credit or reward points.

In an embodiment, at least a portion of the information mark of a subject is configured to be removed by the subject's body (e.g., biodegradation, bioabsorption, etc.). In an embodiment, at least a portion of the information mark of a subject is configured to be removed only through assistance (e.g., chemical treatment, mechanical treatment, chemo-mechanical treatment, pressure, electromagnetic field, surgery, etc.).

In an embodiment, the information mark includes at least one spectral coding. In an embodiment, the information mark includes at least one spatial coding. In an embodiment, the information mark includes multiple dyes or variation of ratios of dyes in order to convey information. In an embodiment, one or more dyes are distinguished by fluorescence or phosphorescence. In an embodiment, one or more dyes are distinguished by temporal or spatial properties. For example, in an embodiment, a combination of dyes and nanoparticles is utilized to increase the combinatorial possibilities for temporal and/or spatial properties. In an embodiment, nanocrystals are utilized for increased stability of the spectral emission. In an embodiment, true phosphors are utilized that have a long (>1/10 sec) storage time, which enables a set of 4-6 "bits" of information from fluorescence while being illuminated, and a second set of "bits" from phosphorescence after the illuminator is turned off. In an embodiment, "fast" and "slow" phosphors are utilized, which allows for 3 "bits," for example, at t=0, t=0.1, and t=1 second. In an embodiment, at least one inorganic pigment or dye is utilized to increase the gradual loss of intensity of the information mark that occurs for most injected dyes. In an embodiment, relative intensities are utilized for encoding information in the information mark. In an embodiment, various individual pigments or nanoparticles that compose a particular dye or coloring agent are utilized in order to encode specific information.

For example, phosphorescent dyes, such as PtOEP (2, 3, 7, 8, 12, 13, 17, 18-octaethyl-21H-porphine platinum (II)), have high-efficiency (>90%) energy transfer from both singlet and triplet states, which allows for much improved light-emission efficiencies. (See, for example, Baldo, et al., Nature, Vol. 395, pp. 151-154, September 1998, which is incorporated herein by reference.) Likewise, phosphorescent nanoparticles, such as iridium (III)tris(2-(4-tolyl)pyridinato-N,$C^2$)(Ir(mppy)3), have been shown to work well with dye-doped polymers to create light-emitting diodes. (See, for example, Madhwal, et al. Phys. Scr. 81, ABSTRACT 2010, online at iopscience.iop.org, visited Apr. 4, 2012, the content of which is incorporated herein by reference). In another example, 2-pyridylazolate chromophores are synthesized with highly emissive, charge-neutral Os, Ru, Ir, and Pt complexes for organic light-emitting diodes. (See, for example, Chou and Chi, Chemistry, Mendeley ABSTRACT, online at mendeley.com/research/phosphorescent-dyes-organic-light-emitting-diodes, visited Apr. 4, 2012, the content of which is incorporated herein by reference). Finally, phosphorescent nanoparticles that shield quenchers, such as oxygen, which results in a stronger signal, have been developed with well-defined luminescent decay times that allow for use in gated measurements, which excludes background fluorescence and enhances signal intensity. (See for example, the catalog page of Active Motif Chromeon, online at chromeon.de/catalog/nanoparticles/phosph_nano, visited Apr. 4, 2012, the content of which is incorporated herein by reference). Thus, many different phosphorescent dyes allow for choices in regard to absorbance, emission, decay time, and conjugation properties of the particle for different uses with embodiments described herein.

In an embodiment, one or more magnetic particles are utilized to form, for example, an array of information about the subject. In an embodiment, the array of magnetic particles includes approximately 20 to approximately 50 magnetic particles, or any value therebetween. In an embodiment, one or more magnetic tattoo particles are injected into the skin of a subject to store information and configured to be read by a health care provider. In an embodiment, the reading of the information includes a process and/or system that links or utilizes the subject's medical health records (including, optionally electronic medical records).

In an embodiment, the information mark is read with magnetic particles that are approximately 5-20 μm apart, approximately 20-100 μm apart, approximately 100-500 μm apart, approximately 500-2000 μm apart, approximately 2-10 mm apart, or any value less than or therebetween.

In an embodiment, the information mark is read with fluorescent particles, phosphorescent particles, or multi-spectral ink depositions that are located approximately 1-5 μm apart, approximately 5-20 μm apart, approximately 20-100 μm apart, approximately 100-500 μm apart, approximately 500-1000 μm apart, or any value less than or therebetween.

In an embodiment, information is stored in analog or digital form in the one or more magnetic particles. In an embodiment, digitally stored information is stored as a single bit per particle, or multiple bits per particle. In an embodiment, a particle can contain multiple closely spaced magnetically readable regions, each encoding one or more bits of data, similar to magnetic storage in hard drives. In an embodiment, the magnetic particles encode information based on magnitude or direction of the associated magnetic fields. In an embodiment, the magnetic particles encode information based on magnetic moments (e.g., dipole, quadrapole, etc.) of the magnetic fields. In an embodiment, the magnetic particles encode information based on the hysteresis or frequency response of magnetic fields. The particles need not initially be magnetized. For example, in an embodiment, information is encoded in response to an external field. In an embodiment, information is encoded in the magnetic response of unmagnetized particles to an external field. For example, in an embodiment, the magnetic response includes magnetic permeability, remnance, hysteresis curve, or frequency response. In an embodiment, the one or more magnetic particles are also colored. In an embodiment, the colored particles are correlated with the magnetic information. In an embodiment, the colored particles are colored to match skin tones, colored in infrared or ultraviolet light, or camouflage the information mark itself.

For example, a magnetic moment as a quantity is determinative of the force that the magnet can exert on electrical currents and the torque that a magnetic field will exert on it (e.g., the magnetic moment is proportional to the magnet's own magnetic field). Both the magnetic moment and the magnetic field are indicated as vectors (having both magnitude and direction). For example, the direction of the magnetic moment points from the south to north pole of a magnet.

In an embodiment, the magnetic information is rewriteable. For example, in an embodiment the information is erased with a magnetic field not ordinarily found in the subject's environment. For example, in an embodiment, the information can be rewritten as indicated by software (e.g., data encoding) or hardware (e.g., indicator particles) and optionally includes one or more certification signals.

In an embodiment, Curie temperature for thermal erasure of tattoo data is employed. For example, particles have individual setpoints for erasure and pulse heating is utilized for erasure of the information and in order to avoid physiological effects.

For example, the Curie temperature or Curie point is the temperature at which a magnet loses its magnetism. For example, a ferrimagnetic or ferromagnetic material becomes reversibly paramagnetic on heating.

In an embodiment, the one or more magnetic particles is colored, as described herein elsewhere. For example, the magnetic particles are colored by infrared or ultraviolet light in an embodiment, in order to be invisible to the naked eye.

As described herein elsewhere, the one or more magnetic particles encode information in a spatial pattern of magnetic tattoo particles (e.g., arrays, symbols, text, fractals, etc.). In an embodiment, a pattern can be formed by 1-D, 2-D, or 3-D fractal dimensions. In an embodiment, as described herein elsewhere, information that is stored includes identification, medical information, timing information, links to information, and/or data files. In an embodiment, information is encrypted.

In an embodiment, indicator particles are utilized in order to identify readout events. In an embodiment, the information mark including one or more magnetic particles is read by a high-sensitivity field sensor. In an embodiment, an array of detectors (e.g., a grid) is utilized to sense the magnetic particle location(s) of the information mark. In an embodiment, one or more paramagnetic particles perturb a magnetic field applied to the subject's skin.

In an embodiment, the one or more magnetic particles include at least one of ferromagnetic, paramagnetic, ferritic, antiferromagnetic, ferromagnetic, metals, ceramics, semiconductors, oxides, etc. In an embodiment, the one or more magnetic particles utilize Curie-temp thermal sensors. In an embodiment, the magnetic particles have different Curie temperature setpoints.

In an embodiment, the information is encoded in a spatial pattern of particles, for example, arrays, symbols, fractals, text, etc. In an embodiment, the spatial pattern incorporates one or more different particles described herein (e.g. ferromagnetic particle and phosphorescent particle). In an embodiment, for example, an information mark includes an array of particles, one or more of which is a magnetic particle, one or more of which is a phosphorescent particle, one or more of which is a Quantum dot, and/or one or more of which is a colorimetric particle.

As shown in FIG. 1, as described elsewhere herein, in an embodiment, to monitor adherence to a treatment plan, a patient is injected in the skin of the wrist with magnetic microparticles containing chromophores, and an inert polymer coating. Magnetic microparticles composed of $Fe_3O_4$, approximately 1 μm in diameter are available from Bangs Laboratories Inc., Fishers, Ind. The magnetic microparticles are coated with chromophores (e.g., FD&C Blue No. 1 and FD&C Red No. 3), to create blue and red magnetic particles, respectively. A transparent, inert, biocompatible coating is applied to protect the particles (e.g., Epo-Tek®301 available from Epoxy Technology, Billerica, Mass.), and the particles are suspended in a carrier such as 20% (w/w) glycerin. The particles may also be non-magnetic, and colored with a chromophore (e.g., FD&C Yellow No. 6), to create yellow particles that are not influenced by a magnetic field. Methods and compositions for creating magnetic tissue markings are described (see e.g., U.S. Pat. No. 7,344,587, which is incorporated herein by reference).

A pattern of colored magnetic markings is injected on the wrist immediately beneath the epidermis of the patient (approximately 100 μm to 300 μm beneath the skin). An oscillating tattoo machine with a needle array may be used to inject the particles (e.g., Spaulding Tattoo Machine available from Spaulding and Rogers, Albany, N.Y.), and create a pattern that encodes dosing information.

A pattern of colored magnetic and nonmagnetic particles is implanted under the patient's epidermis to monitor treatment with multiple drugs. To indicate twice daily dosing with 80 mg of propranolol, two rows of dots (with 7 dots per row) are injected using a mix of magnetic blue particles and nonmagnetic yellow particles, to create green dots. To indicate daily dosing with 15 mg of hydrochlorothiazide, one row of 7 ovals is injected using a mix of magnetic red particles and non-magnetic yellow particles, to create brown ovals. The pattern of magnetic to non-magnetic particles itself can be "read" as containing information, or representing information.

Figure 2:
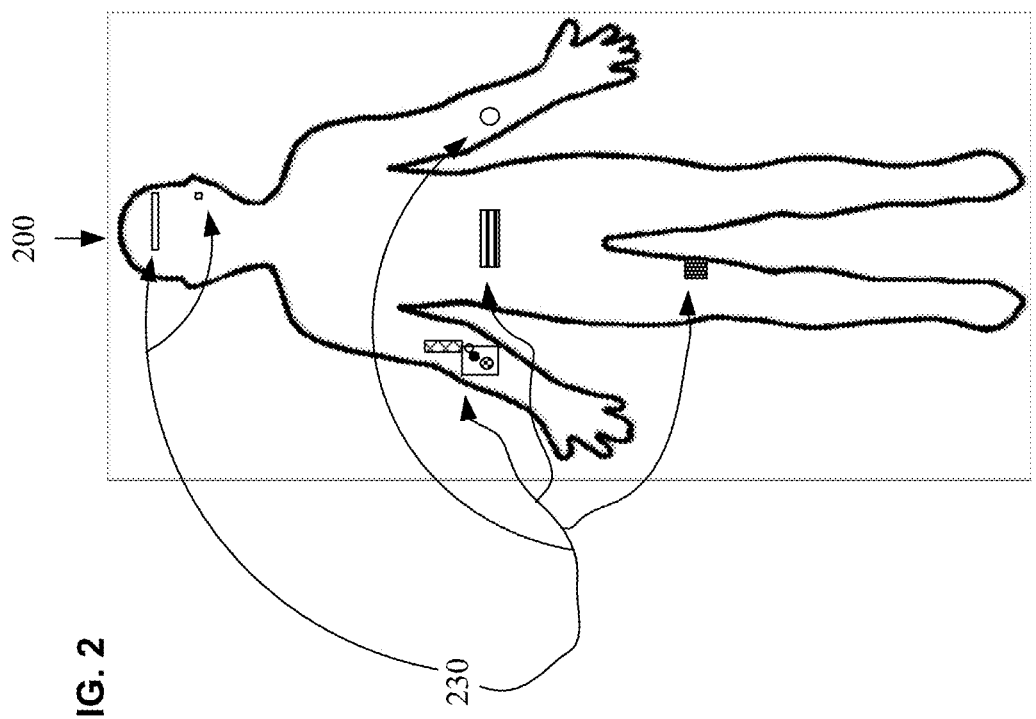
FIG. 2 illustrates a partial view of a particular embodiment described herein.
Figure 2:
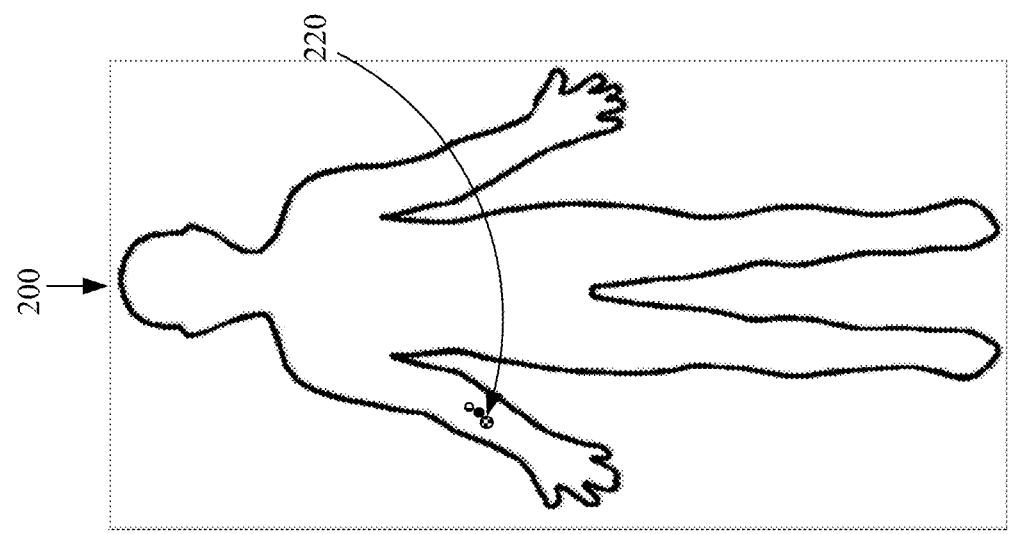

As shown in FIG. 2, a subject 200 has received a series of information marks 220 that become part of a larger pattern of representation when the subject 200 receives additional information marks as a result of further medical treatment. Thus, in an embodiment, additional information is included in the additional information marks, as well as in the pattern as a whole, resulting in a combinatorial increase in representation of information by the information marks.

Figure 3:
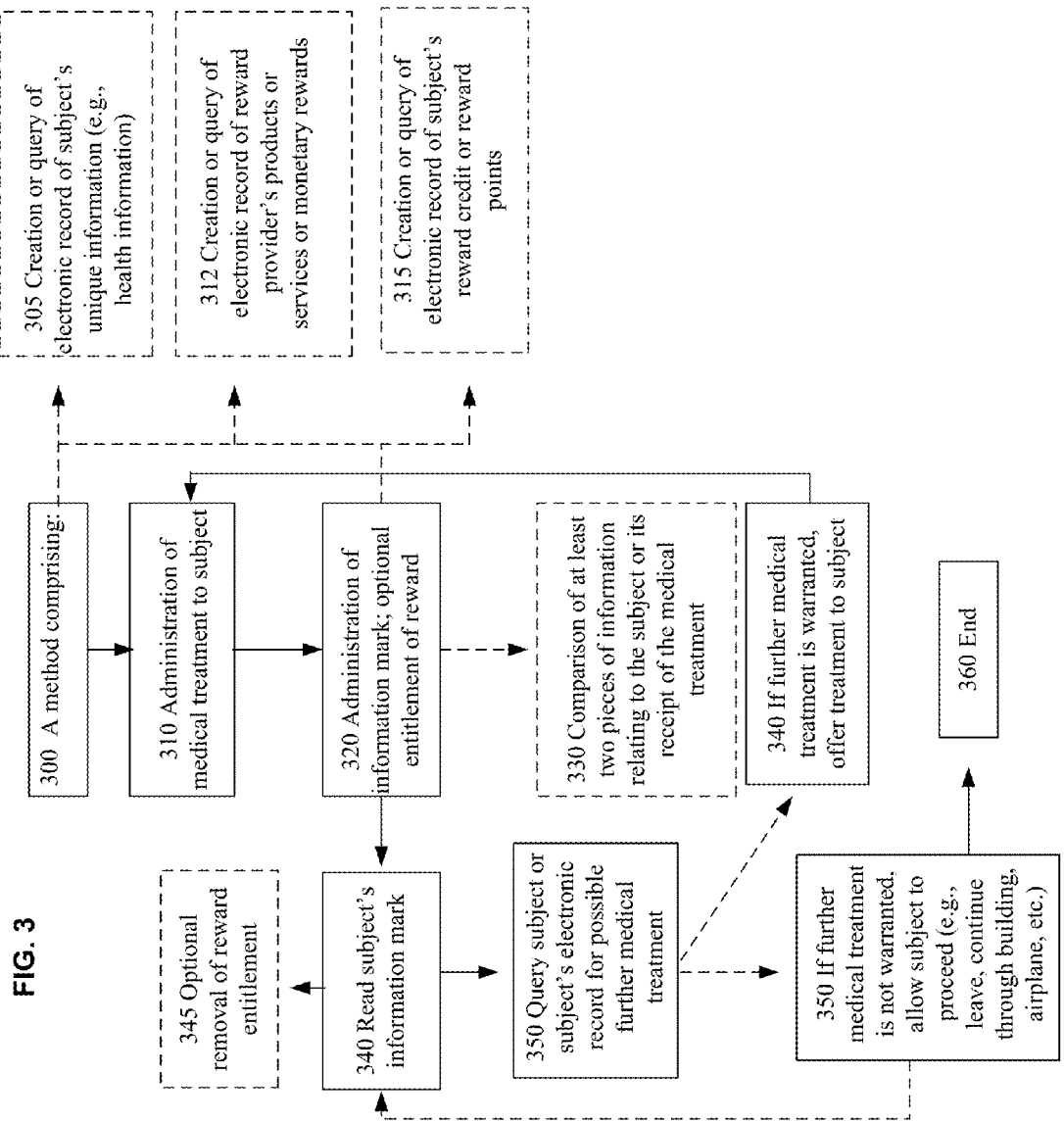
FIG. 3 illustrates a partial view of a particular embodiment described herein.

As depicted in FIG. 3, in an embodiment, a method 300 includes administration 310 of medical treatment (e.g., at least one therapeutic agent) to a subject; administration 320 of an information mark and optional entitlement of reward; optional comparison 330 of at least two parcels of information relating to the subject or its receipt of the therapeutic agent or other medical treatment; and a decision that 340 if further medical treatment is warranted, then treatment is offered to the subject. In an embodiment, following administration 320 of an information mark and optional entitlement of reward, the subject's information mark can be read 340. In an embodiment, subsequent to "reading" the subject's information mark, the subject or subject's electronic record can be queried 350 for possible further medical treatment, and optionally, if further medical treatment is not warranted 350, then the subject is allowed to proceed (e.g., leave, continue through the building, airplane, etc.), and optionally return to read the subject's information mark again 340. Optionally, in an embodiment, creation or query 305 of an electronic record of subject's unique information (e.g., health information) can occur prior to administration of medical treatment to a subject, during administration of medical treatment to a subject, or subsequent to administration of medical treatment to a subject. Optionally, in an embodiment, creation or query 312 of an electronic record of a reward provider's products or services, or other monetary rewards can occur prior to administration of medical treatment to a subject, during administration of medical treatment to a subject, or subsequent to administration of medical treatment to a subject. Optionally, in an embodiment, creation or query 315 of electronic record of a subject's reward credit or reward points can occur prior to administration of medical treatment to a subject, during administration of medical treatment, or subsequent to administration of medical treatment to a subject.

Figure 4:
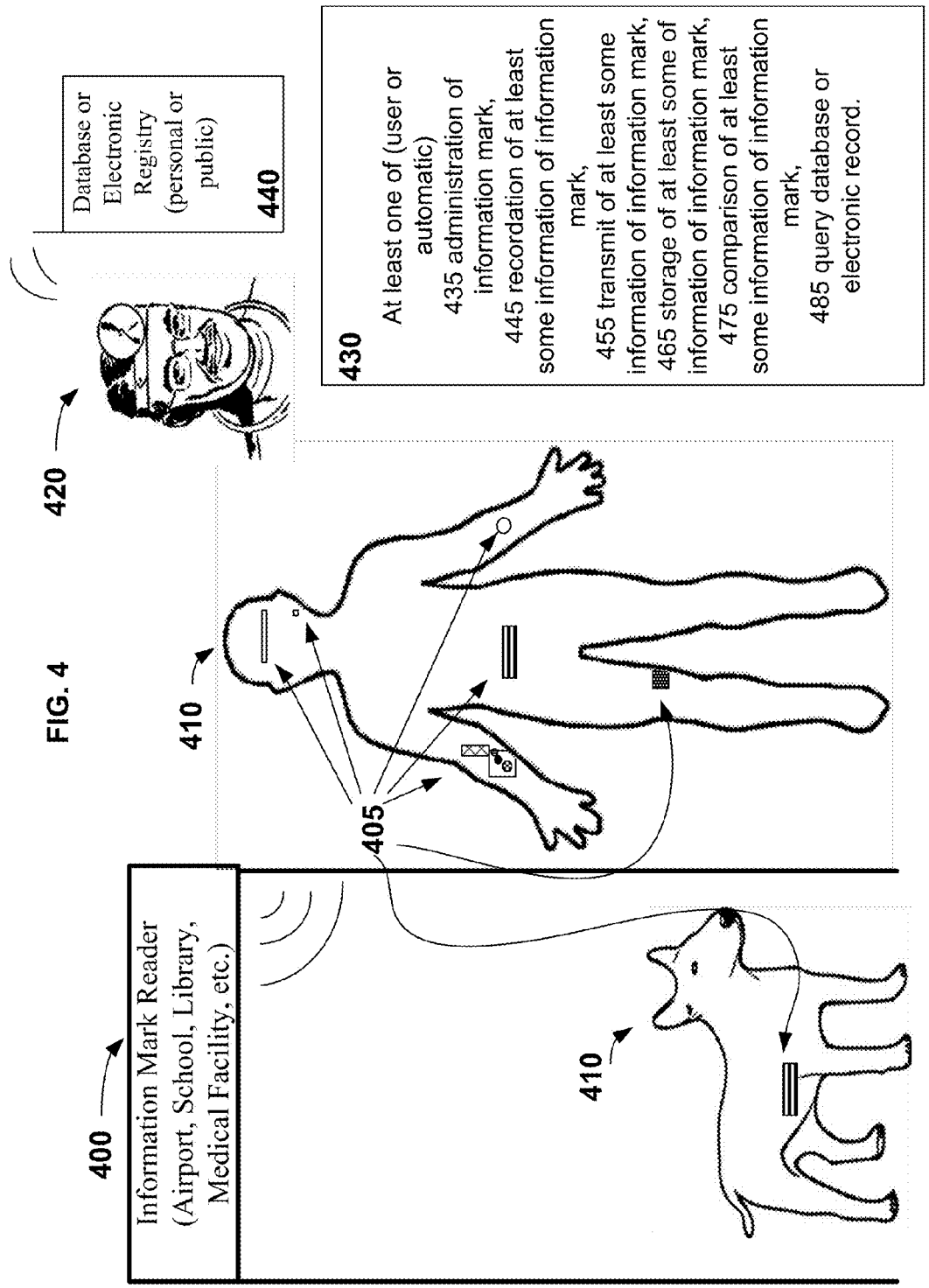
FIG. 4 illustrates a partial view of a particular embodiment described herein.

As shown in FIG. 4, a subject 410 who has received at least one information mark 405, passes near or through an information mark reader 400 (located, for example, at an airport, school, library, medical facility, etc.) and at least some of the information is read. In an embodiment, the information mark reader 400 (e.g., camera, fluorescent receiver, etc.) is operably coupled with a device configured to administer at least one information mark, and/or at least one therapeutic agent. In an embodiment, at least one of the following method steps 430 occurs (automatically, or manually entered by a user): administration 435 of an information mark; recordation 445 of at least some information of an information mark (e.g., at least one parcel of information); transmission 455 of at least some information of an information mark (e.g., at least one parcel of information); storage 465 of at least some information of an information mark; comparison 475 of at least some information of an information mark; or query 485 of database or electronic record of the subject (or public electronic registry) 440. In an embodiment, a health care professional 420 locally or remotely receives information related to the information mark(s) of the subject and optionally offers additional medical treatment (e.g., vaccination) if it is deemed to be warranted. If no further medical treatment is deemed to be warranted, the subject is allowed to proceed. In an embodiment, the information mark reader 400 includes at least one receiver 560.

Figure 5:
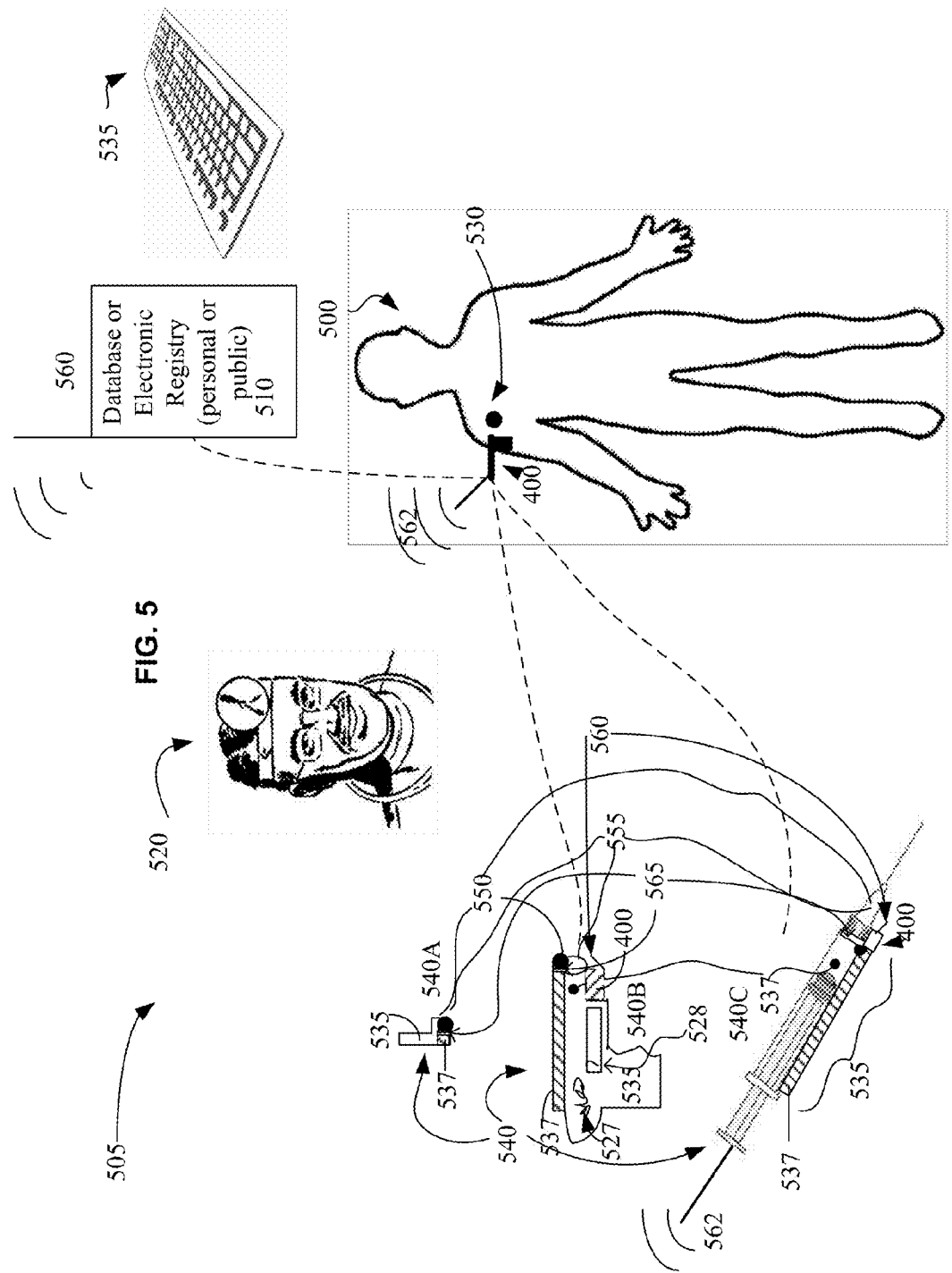
FIG. 5 illustrates a partial view of a particular embodiment described herein.

As depicted in FIG. 5, in an embodiment, a system 505, includes a device 540 includes a housing 535, at least one first chamber 537 for containing the at least one information mark, at least one second chamber 538 for containing the at least one therapeutic agent, and means for administering 550 at least one information mark 530 to a subject 500. In an embodiment, an information mark reader 400 includes means for receiving and/or transmitting at least one information signal from the information mark. In an embodiment, the device includes means for administering 555 at least one therapeutic agent. In an embodiment, the means for administering 550 at least one information mark is the same as the means for administering 555 at least one therapeutic agent (540C, 540A). In an embodiment, the means for administering 550 at least one information mark is different than the means for administering 555 at least one therapeutic agent. In an embodiment, the device 540 includes at least one controllable output mechanism 565 for administering at least one information mark. In an embodiment, (540B, 540C) the at least one information mark is contained in a separate chamber as the at least one therapeutic agent. In an embodiment (540A) the at least one information mark is contained in the same chamber as the at least one therapeutic agent. In an embodiment, the at least one information mark 530 is administered to the surface of the subject 500 (e.g., skin). In an embodiment, the at least one information mark 530 is administered below the surface of the subject 500 (e.g., subdermally, subcutaneously, intra-muscularly, etc.). In an embodiment, the at least one controllable output mechanism for administering at least one information mark 565 is the same as the at least one controllable output mechanism for administering at least one therapeutic agent (e.g., see 540A, and 540C). In an embodiment, the at least one controllable output mechanism for administering at least one information mark 565 is different than the at least one controllable output mechanism for administering at least one therapeutic agent (e.g., 540B, 555, 565). In an embodiment, the means for administration of the at least one information mark 550 or at least one therapeutic agent includes at least one of a spring mechanism (527 of 540B), compressed gas (540A), or a power source mechanism (e.g., a battery) (not shown). In an embodiment (528 of 540B), a trigger mechanism or other activation switch (not shown) dispenses at least one of the information mark or the therapeutic agent.

In an embodiment, the device 540 includes an electronic circuit system configured to be electrically coupled to the means for administering 550 at least one information mark. In an embodiment, the device 540 includes an electronic circuit system configured to be electrically coupled to the at least one controllable output mechanism 565.

In an embodiment, the device 540 can be any device suitable for administering at least one therapeutic agent or at least one information mark to a subject's body. In an embodiment, such device 540, includes but is not limited to auto-injectors, inhalers (540A), pen injectors, transdermal patches, pre-filled syringes, syringes (540C), catheters, vaccination guns (540B), stents, implantable vehicles, topical vehicles, pill dispensers, or other devices.

As described herein, the device 540 includes, in an embodiment, electronic circuitry for execution of various functions and activation of particular features described herein.

Also as described herein, in an embodiment, the device 540 includes a wireless communications system 562 configured to automatically transmit at least one parcel of information to another device, computer system, or electronic registry. In an embodiment, such wireless communication system 562 is configured to track subject compliance with medication administration (self-administration or administration by another entity).

In an embodiment, a health care provider 520 administers the information mark 530 just prior to, during, or subsequent to administration of other medical treatment (e.g., vaccination by a syringe or gun as indicated by 540, or inhaler, also 540). In an embodiment, at least some of the information included in the information mark 530 is transmitted 562, recorded, or stored in a database or electronic registry (personal or public) 510. In an embodiment, an input/output device 535 allows for entry of inputs by a user or for the presentation of information to the user. In an embodiment, a receiver 560 is configured to receive an information signal from the information mark 530. In an embodiment, the means for administering 550 at least one information mark 530 is further configured as means for "reading" at least one information mark 530.

Figure 6:
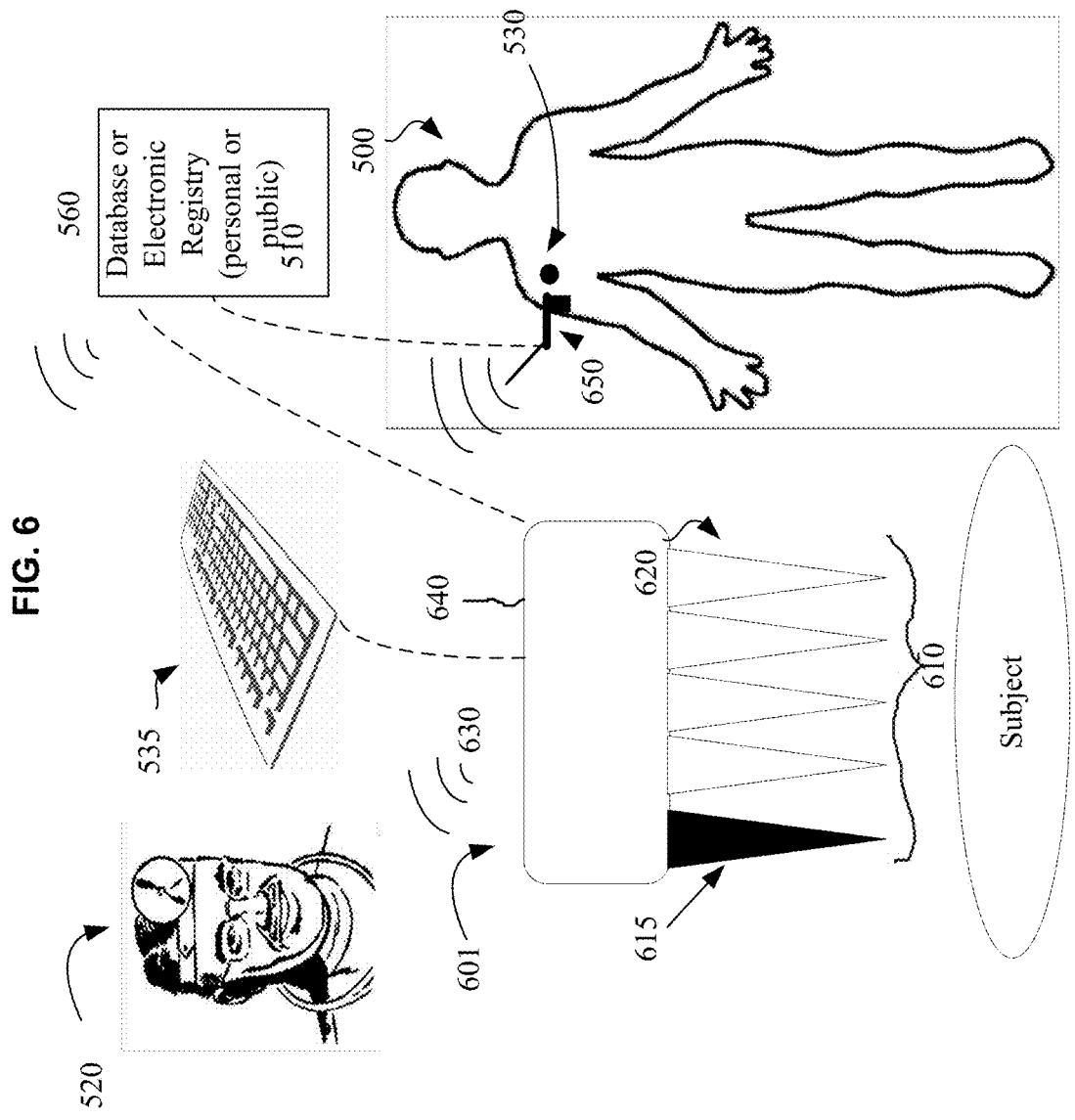
FIG. 6 illustrates a partial view of a particular embodiment described herein.

In an embodiment, as shown in FIG. 6, a programmable selector device 601, comprises electrical circuitry configured for selecting at least one energy absorbance component 615 and at least one energy transmission component 620 of a multi-spectral ink; two or more fluid chambers 610, wherein each component is in a separate fluid chamber; the electrical circuitry further configured for indicating each selection by one or more signals 630. In an embodiment, the one or more signals 630 include at least one of an optical, audio, or tactile signal. In an embodiment, the fluid chamber includes at least one of a needle or spray injector. In an embodiment, the at least one energy absorbance component and the at least one energy transmission component include different wavelengths of activation. In an embodiment, the two or more fluid chambers are spatially separated. In an embodiment, the two or more fluid chambers are spatially separated based on a pre-determined pattern or other arrangement. In an embodiment, the pre-determined pattern or other arrangement includes an ordered sequence of administration of each selection. In an embodiment, the pre-determined pattern or other arrangement includes a linear pattern. In an embodiment, the pre-determined pattern or other arrangement is customizable for a subject. In an embodiment, the device is programmable to administer to a subject one or more combinations of each selection (shown). In an embodiment, the two or more fluid chambers are temporally separated in function. In an embodiment, the two or more fluid chambers are configured to administer a reference calibration mark to the subject. In an embodiment the two or more fluid chambers are pre-filled. In an embodiment, the device includes at least one transmitter, receiver, or transceiver (640). In an embodiment, the one or more of the transmitter, receiver, or transceiver is wireless. In an embodiment, the electrical circuitry is configured to communicate with one or more computing devices.

In an embodiment, the at least one energy absorbance component and the at least one energy transmission component are selected such that, following administration, the at least one energy transmission component transfers energy to the at least one energy absorbance component. In an embodiment, the device is handheld. In an embodiment, the device is included as part of a decal, bandage, or iontophoretic device. In an embodiment, the programmable selector device further comprises re-usable fluid chambers. In an embodiment, the programmable selector device further comprises one or more reservoirs in fluid communication with the two or more fluid chambers.

As described in FIG. 5, in an embodiment, the programmable selector device likewise, is utilized by a health care provider 520 to administer the information mark 530 to a subject 500 just prior to, during, or subsequent to administration of other medical treatment. In an embodiment, at least some of the information included in the information mark 530 is transmitted 562, recorded, or stored in a database or electronic registry (personal or public) 510. In an embodiment, an input/output device 535 allows for entry of inputs by a user or for the presentation of information to the user. In an embodiment, a receiver 560 is configured to receive an information signal from the information mark 530. In an embodiment, the means for administering 550 at least one information mark 530 is further configured as means for "reading" at least one information mark 650.

In an embodiment, at least one component has an energy absorbance in the range of approximately 400 nm-approximately 700 nm. In an embodiment, at least one component has an energy absorbance in the range of approximately 10 nm-approximately 400 nm. In an embodiment, at least one component has an energy absorbance in the range of approximately 0.74 µm-approximately 300 µm.

In an embodiment, at least one component has an energy transmission in the range of approximately 400 nm-approximately 700 nm. In an embodiment, at least one component has an energy transmission in the range of approximately 10 nm-approximately 400 nm. In an embodiment, at least one component has an energy transmission in the range of approximately 0.74 µm-approximately 300 µm. One of skill in the art would understand that if energy transference is desired between the energy transmission component and the energy absorbance component, that in a given embodiment, transmission and absorbance wavelengths would be different. For example, an energy transmission of approximately 700 nm may be absorbed by a component, while other energy wavelengths are not. Thus, the components can each be designed with specificity for energy transference.

For example, in an embodiment, one or more light emitters and/or light sources may be configured to provide for upconversion of energy. In an embodiment, infrared light may be upconverted to visible light (e.g., Mendioroz et al., Optical Materials, 26:351-357 (2004). In an embodiment, infrared light may be upconverted to ultraviolet light (e.g., Mendioroz et al., Optical Materials, 26:351-357 (2004). In an embodiment, one or more light sources may include one or more rare-earth materials (e.g., ytterbium-erbium, ytterbium-thulium, or the like) that facilitate upconversion of energy (e.g., U.S. Pat. No. 7,088,040; herein incorporated by reference). For example, in an embodiment, one or more light sources may be associated with Nd3+ doped KPb2C15 crystals. In an embodiment, one or more light sources may be associated with thiogallates doped with rare earths, such as CaGa2S4:Ce3+ and SrGa2S4:Ce3+. In an embodiment, one or more light sources may be associated with aluminates that are doped with rare earths, such as YAlO3:Ce3+, YGaO3:Ce3+, Y(Al,Ga)O3:Ce3+, and orthosilicates M2SiO5:Ce3+ (M:Sc, Y, Sc) doped with rare earths, such as, for example, Y2SiO5:Ce3+. In an embodiment, yttrium may be replaced by scandium or lanthanum (e.g., U.S. Pat. Nos. 6,812,500 and 6,327,074; herein incorporated by reference). Numerous materials that may be used to upconvert energy have been described (e.g., U.S. Pat. Nos. 5,956,172; 5,943, 160; 7,235,189; 7,215,687; herein incorporated by reference).

Figure 7:
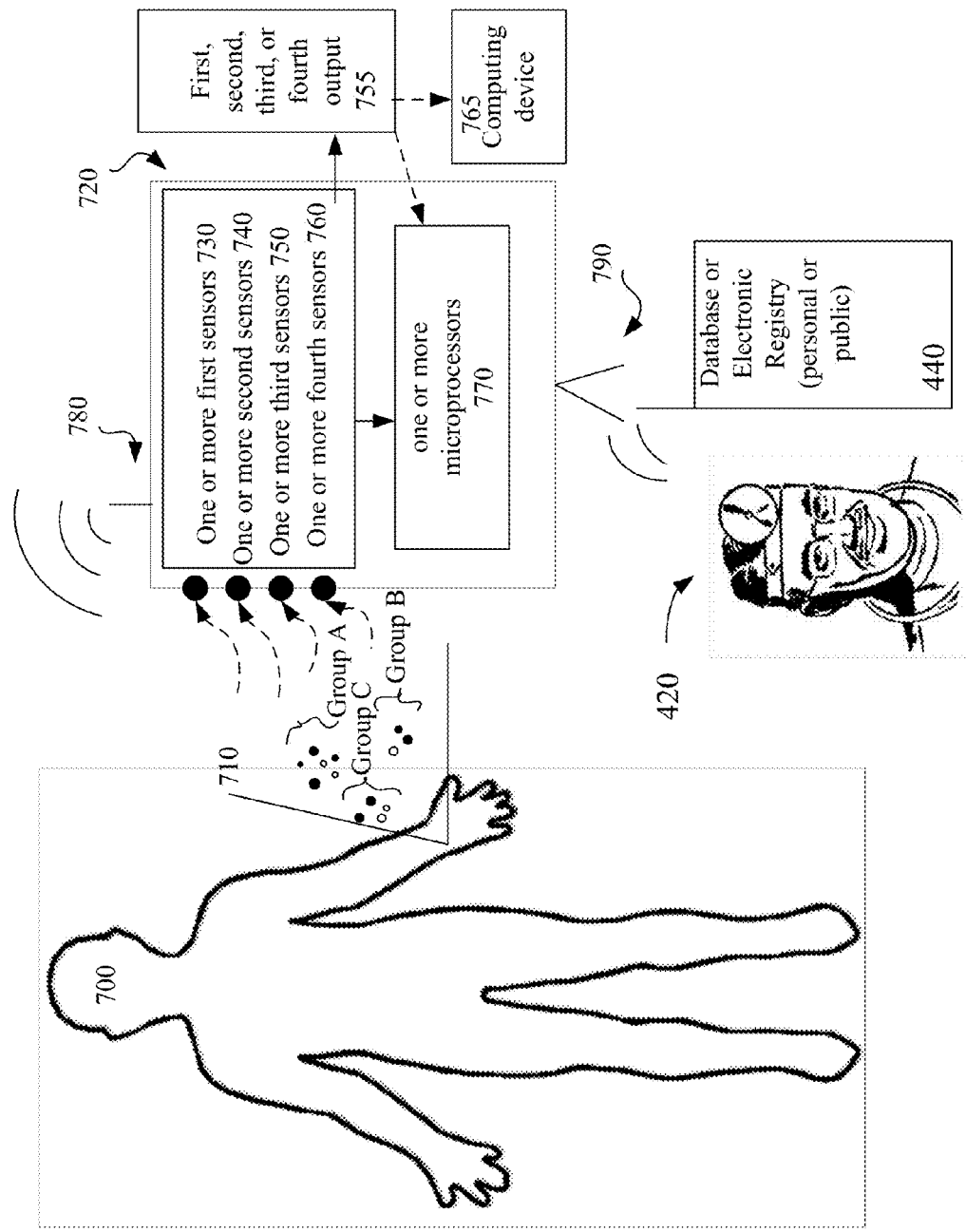
FIG. 7 illustrates a partial view of a particular embodiment described herein.

As described in FIG. 7, a subject 700 has undergone one or more health care visits during which information marks were conveyed to the subject. For example, 710 indicates an enlargement of the subject's wrist area, for which Group A, Group B, and Group C indicate separate information marking designs. Group A indicates various particles combined to form the information mark. In an embodiment, these particles are of different sizes, shapes, some are solid (indicating, for example, that a health care treatment has occurred or is required to occur, depending on what the physician designates for that particle), some are open circles (indicating, for example with magnetic particles, that the particle has been erased such as for a vaccination requirement that has been satisfied or completed). In an embodiment, the particles constitute various types of materials. For example, in an embodiment, one particle is a magnetic particle, another particle is a phosphorescent particle, another particle is a fluorescent particle, etc. In an embodiment, all of the particles of one information mark (e.g., Group A) are all of one material (e.g., magnetic), while all of the particle of one information mark (e.g., Group B) are all of a different material (e.g., phosphorescent), which lends itself to increased ability to utilize many different combinations for information and still provides distinction between information marks on the subject.

In this particular embodiment, the particles of each Group are arranged in different patterns, each pattern constituting in this embodiment, separate information marks. In an embodiment, the spatial pattern of the information mark includes particles that are approximately 5 to 10 μm apart, approximately 10 to 20 μm apart, approximately 20 to 50 μm apart, or any value less than or therebetween, and is indicative of the particles being part of the same information mark. In an embodiment, particles or groups of particles that are approximately 50 μm to 100 μm apart, approximately 100 μm to 200 μm apart, approximately 200 μm to 500 μm apart, or any value greater than or therebetween, from other particles or groups of particles are indicative of separate information marks and are read as such.

In an embodiment, one or more particles described herein are encapsulated prior to injecting into a subject. In an embodiment, the encapsulation procedure utilized is similar to drug encapsulation methods that are known in the art. For example, one or more particles are encapsulated in ethylcellulose, methylcellulose, protein (e.g., vaccine or adjuvant), poly (lactic-co-glycolic acid) or PGLA, poly methyl methacrylate or PMMA, a synthetic polymer (e.g., polyesters, poly (ortho esters), polyanhydrides, polyphosphazenes, etc.), a natural polymer (e.g., chitosan, hyaluronic acid, alginic acid, etc.). See for example, Park, et al., Molecules (2005) 10; pp. 146-161, which is incorporated herein by reference. As described, the encapsulation can be performed, for example, by methods including emulsion-solvent evaporation/extraction (e.g., single, or double emulsion). In an embodiment, the encapsulation material is biodegradable or bioresorbable.

In an embodiment, the encapsulated particles further include therapeutic agents such as collagen, elastin, fibrin, fibrinogen, cytokines, anti-inflammatory agents, vitamins, minerals, cell adhesion molecules, or other therapeutic agent to minimize scarring, prevent migration of the particle, or provide dermal or epidermal support. In an embodiment, the encapsulated particle is less than or equal to about 250 nm, less than or equal to about 200 nm, less than or equal to about 150 nm, less than or equal to about 100 nm, less than or equal to about 50 nm, less than or equal to about 25 nm, or less than or equal to about 10 nm, or any value less than or therebetween in size. In an embodiment, the encapsulation is a vehicle for delivery of the information mark particle(s) and includes a colorant (e.g., pigment) of its own, in order to determine confirmation of delivery to the subject. In an embodiment, this colorant is rapidly taken up by the body, or fades or dissipates quickly and does not interfere with the dyes or pigments or other colorants of the actual information mark particle(s).

In an embodiment, one or more particle described herein is not encapsulated, and is less than or equal to about 250 nm, less than or equal to about 200 nm, less than or equal to about 150 nm, less than or equal to about 100 nm, less than or equal to about 50 nm, less than or equal to about 25 nm, or less than or equal to about 10 nm, or any value less than or therebetween in size.

FIG. 7 also indicates an embodiment of a device for reading one or more information marks in a subject 720. In an embodiment, the means for reading at least one information mark in the skin or other biological tissue of a subject 650 includes a programmable reader device 720. In an embodiment, the programmable reader device 720 is coupled with or incorporated with the programmable selector device described herein that is utilized to administer the information mark to the subject. In an embodiment, the programmable reader device includes one or more first sensors 730 configured for sensing the magnetic field of the at least one magnetic particle of an information mark, one or more second sensors 740 configured for sensing the energy field emitted from at least one phosphorescent particle of an information mark, one or more third sensors 750 configured for sensing the energy field emitted from at least one multi-spectral ink deposition of an information mark, one or more fourth sensors 760 configured for sensing the energy field emitted from at least one fluorescent particle of an information mark, and one or more microprocessors 770 configured to process data from the one or more first sensors 730, the one or more second sensors 740, the one or more third sensors 750, and the one or more fourth sensors 760 to determine one or more characteristics associated with the information mark.

As described in FIG. 4, in an embodiment, a health care professional 420 locally or remotely receives information related to the information mark(s) of the subject and optionally offers additional medical treatment (e.g., vaccination) if it is deemed to be warranted. If no further medical treatment is deemed to be warranted, the subject is allowed to proceed. Now, in FIG. 7, further details of an embodiment of an information mark reader 400 are depicted as the programmable reader device 720.

In an embodiment, the programmable reader device 720 further comprises at least one of a transmitter, receiver, or transceiver 780. In an embodiment, at least some information read from the information mark is transmitted or received between the programmable reader device and a database or electronic health registry 440. In an embodiment, at least one of the transmitter, receiver, or transceiver is wireless. In an embodiment, at least one of the transmitter, receiver, or transceiver is in communication with at least one computer device or computer system.

In an embodiment, the programmable reader device includes a guide 790 configured to steady the device for an accurate reading. In an embodiment, the guide 790 includes, for example, at least one of a bi-pod or tri-pod stand (shown), a roller ball (not shown), a fluid leveler gauge to indicate when the device is level (not shown), or a mechanism with multiple movable members that allow for level positioning of the device (not shown). As described in the other Figures, in one embodiment, the information mark reader further includes at least one delivery mechanism (shown, for example, as various embodiments in the other Figures) configured to administer the information mark. Such delivery mechanism can include, for example, a needle, inhaler, transdermal patch, microneedle, needle array, inkjet injector, microprotusion, cannula, or microcannula (See FIGS. 4-6).

In an embodiment, the programmable reader device includes one or more chambers in fluid communication with the at least one delivery mechanism (See FIGS. 4-6). In an embodiment, the one or more chambers are configured for holding the components for the information mark. In an embodiment, each chamber is configured to hold a different component (e.g., fluorescent particle, phosphorescent particle, magnetic particle, multi-spectral ink, etc.). In an embodiment, the one or more chambers are pre-filled.

In an embodiment, the programmable reader device further comprises a computing device 765 optionally having an input (dotted arrows) coupled to a first output of at least one of the one or more first sensors, a second output of at least one of the one or more second sensors, a third output of at least one of the one or more third sensors, and a fourth output of at least one of the one or more fourth sensors, the computing device configured to generate an image of each of the sensed output 755. In an embodiment, the one or more microprocessors are configured to generate an image of one or more sensed output. In an embodiment, the computing device configured to generate an image of one or more sensed output is remote from the programmable reader device. Such remote computing device may be in electronic communication with the programmable reader device, whether, for example, by wireless means or otherwise.

In an embodiment, the one or more first sensors 730, the one or more second sensors 740, the one or more third sensors 750, or the one or more fourth sensors 760 include an optic sensor (not shown). In an embodiment, at least one of the sensors includes a data acquisition device (e.g., a camera) (not shown). In an embodiment, the programmable reader device includes at least two sensing units, each unit defining a sensing axis orthogonal to the other sensing axis (e.g., means configured to indicate coordinates for reading or otherwise indicate the area for reading the information mark).

In an embodiment, the one or more sensors are configured for sensing particles or other information mark components that are located approximately 5-20 micrometers apart, approximately 20-100 micrometers apart, approximately 100-500 micrometers apart, approximately 500-1000 micrometers apart, approximately 1-2 mm apart, approximately 2-10 mm apart, or any value less than or therebetween.

As described in other Figures and throughout the instant application, the information mark reader (including the programmable reader device) is in the form of a handheld wand, wall mounted device, doorway detector, or vehicle structure.

In an embodiment, the one or more characteristics associated with an information mark include at least one of particle intensity, spatial or temporal distribution of particles, type of particle or particles, or the number of particles. In an embodiment, the programmable reader device is configured to be programmable to read information marks in different subjects, in different biological tissues of a subject, different combinations of particles, different intensities of particles, or different configurations of information marks.

Various non-limiting embodiments are described herein as Prophetic Examples.

Prophetic Example 1

Methods and Device for Recording Medical Information in the Skin of a Child Receiving Recommended Vaccines A method using quantum dot microbeads is used to record medical information in the skin of a child who receives childhood vaccines. The child is approximately 1 year old and receives a recommended vaccine for measles, mumps and rubella. During or immediately after vaccination, the child is marked with quantum dot microbeads to indicate the date, the healthcare worker, the location, the vaccine product identity, the manufacturer, and the lot number. Quantum dot microbead markings are detected with a spectrofluorometer detector containing a light source, a photo-receptor for receiving light emitted by the illuminated quantum dots, and a spectroscopic analyzer for comparing variations in the intensity and wavelength of the emitted light. The detector communicates the spectral data to a computer where the data is stored and compared to predetermined spectral data for the quantum dot microbeads and the associated medical information.

The child is injected with vaccines using standard procedures and a marking of quantum dot microbeads is administered using a microneedle array immediately following vaccination. A combination vaccine for measles, mumps and rubella is injected subcutaneously in the arm of the child, according to the manufacturers' instructions (e.g., see M-M-R® II Product Sheet: available from Merck and Co., Inc., Whitehouse Station, N.J., which is incorporated herein by reference). Immediately following vaccination, the child is injected with quantum dot microbeads to record medical information about the vaccination. Microbeads containing quantum dots (ranging from 2-20 nm in diameter) are injected approximately 500 μm to 1000 μm below the skin surface, near the base of the epidermis. Quantum dots of different diameters, composed of CdSe capped with ZnS, emit light of different wavelengths. For example, quantum dots composed of a CdTe core and a CdSe shell may be created with emission wavelengths, ranging between 800 nm and 900 nm. Quantum dots with a diameter of approximately 10 nm are excited by 550 nm wavelength light and emit light at approximately 860 nm wavelength (e.g., see U.S. Pat. No. 7,181,266, which is incorporated herein by reference). Polymeric microbeads containing quantum dots with different diameters will display a composite emission profile composed of different wavelengths of light. The intensity of light emitted at each wavelength is proportional to the number of quantum dots present in the microbead having a particular diameter. Methods to construct optically encoded microbeads containing quantum dots are described (see e.g., Han et al., *Nature Biotechnology* 19: 631-635, 2001, which is incorporated herein by reference). Microbeads containing a mixture of quantum dots are fabricated from polyacrylamide hydrogels. Microbeads are fabricated from 10% (wt. %) acrylamide and 0.2% (wt. %) bisacrylamide, using a microfluidic device to create uniform beads approximately 130 μm in diameter. Methods and a microfluidic device to construct microbeads are described (see e.g., Shibata et al., *Proc. Natl. Acad. Sci. USA* 107: 17894-17898, 2010 which is incorporated herein by reference). Quantum dots with different core to shell dimensions and different diameters are synthesized by established procedures (see, e.g., U.S. Pat. No. 7,181,266 Ibid.) and are incorporated into microbeads at the time of polymerization. Incorporation of quantum dots into the microbeads allows detection of the encapsulated quantum dots injected in the dermis. For example, quantum dots, in dermal tissues, at a local concentration of approximately 1 µM, are detected through the skin (see e.g., Larson et al., *Science* 300: 1434-1436, 2003, which is incorporated herein by reference). Microbeads containing unique mixtures of quantum dots with characteristic emission spectra that vary in wavelength and intensity are injected beneath the epidermis in a pattern using a microneedle array.

Microbeads with unique fluorescent spectral signatures, as determined by a spectrofluorometer (available from Ocean Optics Inc., Dunedin, Fla.), are associated with data about the vaccination and the patient. For example, microbeads containing 1, 2 or 3 different quantum dots may emit light at 1, 2 or 3 wavelengths respectively, when excited by 550 nm light. Data about the microbeads (e.g., fluorescent spectra) are associated with medical information about the vaccine and the patient, and are entered into a computer for storage and future reference. For example:

Microbead 1 with an emission at 750 nm is associated with the M-M-R® II vaccine produced by Merck and Co., lot #XXX, expiration date.

Microbead 2 with emissions at 750 nm and 900 nm is associated with the age of the patient (e.g., 12 months) and the date of vaccination.

Microbead 3 with emissions at 750 nm, 900 nm and 1050 nm is associated with a recommended future vaccination with M-M-R® II vaccine, the recommended age and the recommended date for the future vaccination.

Microbead 4 with emissions at 750 nm, 900 nm (at reduced intensity, e.g., 0-30%) and 1050 nm may be associated with the site of the vaccination (e.g., school, clinic, hospital).

Additional microbeads with unique fluorescent spectral signatures may be fabricated by using quantum dots with distinct emission wavelengths and by varying the quantities of quantum dots so as to vary emission intensities. The use of 3 emission wavelengths and 10 different intensity levels theoretically yields approximately 1000 unique codes (see e.g., Han et al., Ibid.).

Following vaccination, a pattern of microbeads is injected beneath the epidermis of the patient on the wrist, using a microneedle array. Each unique microbead is injected by one microneedle from the array so as to allow detection of the microbead without interference from other microbeads. The microbeads are injected using an applicator comprising a hollow microneedle array that is connected to a reservoir. Hollow microneedle arrays may be fabricated using microfabrication technology adapted from the microelectronics industry. For example, silicon hollow microneedle arrays may be fabricated by etching holes through silicon wafers using deep reactive ion etching and then etching microneedles around the holes. See, e.g., McAllister et al., *Proc. Natl. Acad. Sci. USA,* 100: 13755-13760, 2003, which is incorporated herein by reference. Microneedle arrays (10×10) containing 100 microneedles in an area of 20×20 mm are constructed with conical microneedles, approximately 1000 µm in length and 300 µm in diameter, may be fabricated as shown by McAllister et al., Ibid. Alternatively, hollow microneedles may be fabricated from metals (e.g., Ni or NiFe) or polymers (e.g., polyglycolic acid and poly lactic acid) by using micromolds or by electroplating polymer microneedles with nickel as shown by McAllister et al., Ibid. Hollow microneedle arrays may be connected via a manifold to a mini-pump, to solenoid valve actuators, and to reservoirs containing microbead suspensions. Mini-pumps and solenoid valves are available from Parker-Hannifin, Precision Fluidics Division, Hollis, N.H. An applicator, comprising hollow microneedle arrays, solenoid valve actuators, a minipump, and reservoirs for the microbead suspensions, has a power source and micro-circuitry to control the injection of microbeads into the skin.

The microbead applicator is programmed by medical information entered in the computer to inject the correct, associated microbeads. For example, if a patient who is 12 months old receives the M-M-R® II vaccine and requires a future vaccination with M-M-R® II vaccine in 3 to 5 years, the information is entered into a computer and then transmitted to the applicator where microcircuitry selects the associated microbeads for injection. For example, microbeads 1-4 would be selected (see above for medical information associated with each microbead). Next, the microbead applicator is placed in contact with the patient's wrist and activated by pressing a button, which provides electric current from a lithium battery to drive the selected solenoid actuator valves and minipumps, delivering the selected microbead suspensions through distinct needles on the microneedle array. Each microbead suspension is injected at a separate, distinct position in the microneedle array to allow microbead detection without interference by neighboring microbeads.

Prophetic Example 2

Methods and Device for Detecting Medical Information in the Skin of a Child Entering School A child who is 6 years of age and entering school has his or her vaccination status checked. The child has previously received a first M-M-R® II vaccination, at age 1 year, marked by injection of microbeads beneath the epidermis of the child's wrist. The microbeads encode information about the vaccine, the child's vaccination status, and recommended future vaccinations. To verify the child's vaccination status prior to entering school, the microbeads in the wrist are analyzed with an apparatus placed over the skin that detects the wavelengths and intensities of light emitted from the microbeads. The apparatus includes a light source to illuminate the immediate area over each microbead injection and a photoreceptor that spectroscopically analyzes any emitted light. The apparatus has fiber optics, which transmit excitation wavelengths, such as ultraviolet light, visible light, near infrared light, and infrared light, to a local area over each microbead injection. The apparatus measures fluorescent light emanating through the skin immediately over the implanted microbeads, and records the wavelength and intensity of the emitted light. For example the apparatus may have a xenon light source rated at 300 Watt to excite the implanted microbeads with white light. Light emitted from the microbeads is detected with optical fibers connected to a spectrometer that detects the intensity of light at different wavelengths. An apparatus and methods for use in a dermal tissue comprising a light source, photo-receptor and/or spectral analyzer, as described (see e.g., U.S. Pat. No. 7,647,085, which is incorporated herein by reference). A portable spectrofluorometer, optical fibers, light source and associated software for measuring fluorescent light, are available from Ocean Optics Inc., Dunedin, Fla. (see e.g., the product sheet "Ocean Optics-QE65000-FL Scientific-Grade Spectrometer," which is incorporated herein by reference). Spectral data obtained from the implanted microbeads is transmitted to a computer and compared to reference data for the implanted microbeads. Spectral data is retained for the patient's health record and used for reference when the patient's vaccination status is interrogated.

Spectroscopy of the microbeads implanted in the student's wrist detects 4 different microbeads, each with a unique optical code. For example they may emit fluorescent light as described above (see Prophetic Example 1):

Microbead 1 with an emission at 750 nm

Microbead 2 with emissions at 750 nm and 900 nm

Microbead 3 with emissions at 750 nm, 900 nm and 1050 nm, and

Microbead 4 with emissions at 750 nm, 900 nm (at reduced intensity, e.g., 30%) and 1050 nm.

The spectral data is transmitted to a computer where the associated medical information is stored to translate the optical codes. The student's optical codes indicate that the student has not received a recommended second M-M-R® II vaccination and the school or healthcare provider may recommend the student receive the vaccination prior to entering school.

The student is given a second M-M-R® II vaccination, as required by the school system, and a fifth microbead is injected in the wrist of the student. Microbead 5 which emits light at 750 nm, 900 nm and 1050 nm (at reduced intensity, e.g., 30%) is associated with the second M-M-R® II vaccination including manufacturer, lot number, and expiration date. Additional microbeads with unique optical codes may be injected and associated with the vaccination date, recommended age for vaccination, age of the patient, name or position of healthcare worker administering the vaccine, and the site where vaccination occurred (e.g., the school, clinic, or office).

Prophetic Example 3

Methods and Device for Monitoring Psychiatric Treatment

A patient with bipolar disorder is prescribed anti-psychotic medication to control the patient's mood, and markings are placed under the patient's skin to indicate administration of the medication. The patient is treated for acute mania and placed on a maintenance regimen of an atypical antipsychotic. After each daily dose, the patient is injected on the wrist with optically encoded quantum dots using a microneedle array. The quantum dots are incorporated in microbeads, which are injected just beneath the epidermis. The quantum dots are detected with a fluorospectrometer, and the fluorescent spectra are transmitted to a computer for decoding. The optically encoded quantum dots indicate to a caregiver the medications administered, the dates of administration, and future recommended doses, as well as patient-specific information.

The patient with bipolar disease is given an antipsychotic daily to control his or her mood, and a marking of quantum dot microbeads is administered each day using a microneedle array. A maintenance regimen of 30 mg daily of the antipsychotic aripiprazole (also known as Abilify® available from Bristol-Myers Squibb, New York, N.Y.) is given to the patient (see e.g., Keck et al., *J. Clin. Psychiatry* 68: 1480-1491, 2007, which is incorporated herein by reference). Immediately following administration of each dose, the patient is injected with microbeads containing quantum dots to record medical information about the medication and the patient. Microbeads containing quantum dots (ranging from 2-20 nm in diameter) are injected approximately 300 µm to 1000 µm below the skin surface near the base of the epidermis. Quantum dots of different diameters emit light of different wavelengths. For example, quantum dots composed of a CdTe core and a CdSe shell may be created with emission wavelengths ranging between 800 nm and 900 nm. Quantum dots with a diameter of approximately 10 nm may be excited by 550 nm wavelength light and emit light at approximately 860 nm wavelength (e.g., see U.S. Pat. No. 7,181,266, which is incorporated herein by reference). Polymeric microbeads containing quantum dots with different diameters will display a composite emission profile composed of different wavelengths of light. The intensity of light emitted at each wavelength is proportional to the number of quantum dots having a particular diameter that are present in the microbead. Methods to construct optically encoded microbeads containing quantum dots are described (see e.g., Han et al., *Nature Biotechnology* 19: 631-635, 2001, which is incorporated herein by reference). Microbeads containing a mixture of quantum dots may be fabricated from polyacrylamide hydrogels. Microbeads are fabricated from 10% (wt. %) acrylamide and 0.2% (wt. %) bisacrylamide, using a microfluidic device to create uniform beads approximately 130 µm in diameter. Methods and a microfluidic device to construct microbeads are described (see e.g., Shibata et al., *Proc. Natl. Acad. Sci. USA* 107: 17894-17898, 2010, which is incorporated herein by reference). Quantum dots with different core to shell dimensions and different diameters are synthesized by established procedures (see e.g., U.S. Pat. No. 7,181,266 Ibid.) and incorporated into microbeads at the time of polymerization. Incorporation of quantum dots into the microbeads allows detection of the encapsulated quantum dots injected in the dermis. For example, quantum dots in dermal tissues, at a local concentration of approximately 1 µM, are detected through the skin (see e.g., Larson et al., *Science* 300: 1434-1436, 2003, which is incorporated herein by reference). Microbeads containing unique mixtures of quantum dots with characteristic emission spectra that vary in wavelength and intensity are injected beneath the epidermis in a pattern using a microneedle array.

Microbeads with unique fluorescent spectral signatures as determined by a spectrofluorometer (available from Ocean Optics Inc., Dunedin, Fla.) are associated with data about administration of medication and the patient. For example, microbeads containing 1, 2 or 3 different quantum dots may emit light at 1, 2 or 3 wavelengths respectively, when excited by 550 nm light. Microbeads with unique fluorescent spectral signatures may be fabricated by using quantum dots with distinct emission wavelengths, and by varying the quantities of quantum dots so as to vary emission intensities. The use of 3 emission wavelengths and 10 different intensity levels theoretically yields approximately 1000 unique codes (see e.g., Han et al., Ibid.). Data about the microbeads (e.g., fluorescent spectra) are associated with medical information about the drug(s) administered, including the dose, date of administration, and the patient's identity. The fluorescent spectra and associated medical information are entered into a computer for storage and future reference. For example, a microbead with a unique fluorescence spectra may be associated with each day's dose of aripiprazole by associating the date, drug, and patient identity with a unique microbead each day.

For example, following administration of 30 mg of aripiprazole, approximately 20 µl of a suspension of a unique microbead, containing quantum dots, at a final concentration of 10 µM, is injected beneath the epidermis of the patient on the wrist using a microneedle array. Each microbead suspension is injected by one microneedle from the array, so as to allow detection of the microbead without interference from other microbeads. The microbeads are injected using an applicator comprising a hollow microneedle array that is connected to a reservoir. Hollow microneedle arrays may be fabricated using microfabrication technology adapted from the microelectronics industry. For example, silicon hollow microneedle arrays may be fabricated by etching holes through silicon wafers using deep reactive ion etching and then etching microneedles around the holes. See, e.g., McAllister et al., *Proc. Natl. Acad. Sci. USA*, 100: 13755-13760, 2003, which is incorporated herein by reference.

Microneedle arrays (10×10) containing 100 microneedles in an area of 20×20 mm are constructed with conical microneedles approximately 100 μm to 1000 μm in length and 300 μm in diameter may be fabricated as shown by McAllister et al., Ibid. Alternatively, hollow microneedles may be fabricated from metals (e.g., Ni or NiFe) or polymers (e.g., polyglycolic acid and poly lactic acid) by using micromolds or by electroplating polymer microneedles with nickel, as shown by McAllister et al., Ibid. Hollow microneedle arrays may be connected via a manifold to a mini-pump, to solenoid valve actuators, and to reservoirs containing microbead suspensions. Mini-pumps and solenoid valves are available from Parker-Hannifin, Precision Fluidics Division, Hollis, N.H. An applicator, comprising hollow microneedle arrays, solenoid valve actuators, a minipump, and reservoirs for the microbead suspensions, has a power source and micro-circuitry to control the injection of microbeads into the skin.

The microbead applicator is programmed to inject the correct, associated microbead. For example, if the psychiatric patient A receives 30 mg aripiprazole on Tuesday, May 3, 2011, the information is entered into a computer and then transmitted to the applicator, where microcircuitry selects the associated microbead for injection. The selected microbead suspension is injected from a unique address in the microneedle array. The microbead applicator is placed in contact with the patient's wrist and activated by pressing a button, which provides electric current from a lithium battery to drive the selected solenoid actuator valves and minipumps, delivering the selected microbead suspension. Each microbead suspension is injected at a separate, distinct position in the microneedle array to allow microbead detection independent from that of neighboring microbeads.

To verify that patient A has received his or her apiprazole today or any previous day, the microbeads in the patient's wrist are analyzed with an apparatus placed over the skin that detects the wavelengths and intensities of light emitted from the implanted microbeads. The apparatus includes a light source to illuminate the immediate area over each microbead injection and a photoreceptor which spectroscopically analyzes any emitted light. For example, the apparatus may have a xenon light source rated at 300 Watt to excite the implanted microbeads with white light. The apparatus has fiber optics which transmit excitation light to a local area over each microbead injection. The apparatus measures fluorescent light, for example at 850 nm, emanating from the microbead through the skin immediately over the implanted microbead, with optical fibers connected to a spectrometer. The spectrometer transmits the wavelength and intensity data of the emitted light to a computer, where the optical code is translated to the corresponding medical information. An apparatus and methods for use in a dermal tissue comprising a light source, photo-receptor, and spectral analyzer as described (see e.g., U.S. Pat. No. 7,647,085, which is incorporated herein by reference). A portable spectrofluorometer, optical fibers, light source, and associated software for measuring fluorescent light, are available from Ocean Optics Inc., Dunedin, Fla. (see e.g., the product sheet: "Ocean Optics-QE65000-FL Scientific-Grade Spectrometer" which is incorporated herein by reference). Spectral data obtained from the implanted microbeads is transmitted to a computer and compared to reference data for the implanted microbeads. Spectral data is retained for the patient's health record, and used for reference when the patient's medication status is interrogated.

Prophetic Example 4

Methods and Device for Monitoring Adherence to Antihypertensive Therapy

An elderly patient with chronic hypertension is prescribed antihypertensives. To monitor the patient's adherence to the treatment plan, the patient is marked with a magnetic marking system to record information on the patient's body that indicates the status of medications administered. The magnetic marking system is composed of magnetic particles that are implanted in the skin in a pattern that can be detected visually and with a laser scanner. The magnetic particles are moved in the skin using a strong magnet to change the color pattern of the particles, and past, present and future doses of medication are indicated by the pattern of the particles.

The patient is prescribed a treatment plan to control hypertension and is provided with a magnetic marking system to monitor adherence to the treatment plan. To control hypertension, a "beta blocker", propranolol, is prescribed as 80 mg tablets to be taken twice a day, and a diuretic, hydrochlorothiazide, is prescribed as 12.5 mg tablets taken once a day. (See FIG. 1).

To monitor adherence to the treatment plan, the patient is injected in the skin of the wrist with magnetic microparticles containing chromophores and having an inert polymer coating. Magnetic microparticles composed of $Fe_3O_4$, approximately 1 μm in diameter, are available from Bangs Laboratories Inc., Fishers, Ind. The magnetic microparticles are coated with the chromophores FD&C Blue No. 1 and FD&C Red No. 3 to create blue and red magnetic particles, respectively. A transparent, inert, biocompatible coating (e.g., Epo-Tek®301 available from Epoxy Technology, Billerica, Mass.) is applied to protect the particles, and the particles are suspended in a carrier such as 20% (w/w) glycerin. The particles may also be non-magnetic, and may be colored with a chromophore (e.g., FD&C Yellow No. 6) to create yellow particles that are not influenced by a magnetic field. Methods and compositions for creating magnetic tissue markings are described (see e.g., U.S. Pat. No. 7,344,587, which is incorporated herein by reference).

A pattern of colored magnetic markings is injected on the wrist immediately beneath the epidermis of the patient (approximately 100 μm to 300 μm beneath the skin). An oscillating tattoo machine with a needle array (e.g., Spaulding Tattoo Machine available from Spaulding and Rogers, Albany, N.Y.) may be used to inject the particles and create a pattern that encodes dosing information.

A pattern of colored magnetic and nonmagnetic particles is implanted under the patient's epidermis to monitor treatment with multiple drugs. To indicate twice daily dosing with 80 mg of propranolol, two rows of dots (with 7 dots per row) are injected using a mix of magnetic blue particles and nonmagnetic yellow particles to create green dots. To indicate daily dosing with 15 mg of hydrochlorothiazide, one row of 7 ovals is injected using a mix of magnetic red particles and non-magnetic yellow particles to create brown ovals. (See FIG. 1).

To indicate administration of a dose of propranolol, a handheld electromagnet is passed over a single green dot (e.g., green dot 1 in row 1 in FIG. 1) to cause migration of the blue magnetic particles within the dot, thereby revealing a yellow dot. Thus, the first dose of propranolol has been consumed on the first day of the week (e.g., designated Monday). Methods and devices to move magnetic particles within the skin are described (see U.S. Pat. No. 7,344,587, Ibid.). To indicate administration of hydrochlorothiazide on the first day of the week, the electromagnet is passed over the first brown oval, thus moving the red magnetic particles and revealing a yellow oval. Administration of succeeding doses of propranolol and hydrochlorothiazide are accompanied by application of the electromagnet to the corresponding dots and ovals, respectively. Visual inspection of the magnetic markings identifies the status of the treatment plan.

After 7 days of complete adherence to the treatment plan, all dots and ovals should be yellow. The following week, administration of propranolol and hydrochlorothiazide are indicated by applying a magnetic field to return the blue and red magnetic particles over the yellow dots and ovals, to create green dots and brown ovals respectively.

The colored markings in the skin may be detected by a device that detects light absorbed and/or reflected from the markings and transmits the resulting cumulative data to a computer system for storage and analysis. A CCD camera may be used to capture images of the colored markings, and to transmit the images of the markings to a computer. Methods and devices for detecting chromophores in dermal tissue are described (see e.g., U.S. Pat. No. 7,647,085, Ibid.). For example, the green dots and brown ovals indicating treatment with anti-hypertensive drugs can be imaged with a CCD camera, e.g., a QIClick Digital CCD Camera available from Q Imaging, Surrey, BC, Canada (see a QIClick datasheet, which is incorporated herein by reference), connected to a computer. Images of the colored tissue markings are captured and analyzed by the computer system and the date, time, and medications administered are stored in the computer with the images. The computer system also stores the treatment plan, as well as past and present doses of medication that are administered. Based on current images of the magnetic markings, the computer system also predicts future doses of medication.

Prophetic Example 5

Device and Methods for Recording and Rewarding Vaccination

A subject is vaccinated with an influenza vaccine, and a marking is made in the skin with a dielectric ink to identify the subject and to record the vaccination. The dielectric ink is detected using handheld sensors to detect microwaves reflected from the dielectric ink pattern. Signals from the sensor are relayed to a computer and analyzed to verify that the subject has been vaccinated and is entitled to a reward. The device and methods are useful for monitoring adherence to a treatment plan, to plan additional vaccinations, and/or to activate a reward system for compliance with the vaccination protocol.

An elderly subject is vaccinated with a seasonal influenza vaccine and marked with a dielectric ink to record medical information in the skin about the vaccine. The vaccine is injected with a microneedle as described (See e.g., Holland et al., J. Inf. Dis. 198: 650-658, 2008, which is incorporated herein by reference). The intradermal vaccine may be a trivalent inactivated split-virion influenza vaccine formulated according to season-appropriate strain recommendations (e.g., A/New Caledonia/20/99 [H1N1], A/Wellington/1/2004 [H3N2], and B/Jiangsu/10/2003), from monovalent lots generally used to prepare the licensed vaccine Vaxigrip (Sanofi Pasteur, Swiftwater, Pa.). The intradermal vaccine, also produced by Sanofi Pasteur (Swiftwater, Pa.), contains approximately 15 to 21 µg of hemagglutinin (HA) per strain per 0.1-mL dose, and is administered in the deltoid region using the BD Microinjection System (Becton Dickinson, Franklin Lakes, N.J.).

Immediately after microinjection of the influenza vaccine, a dielectric ink marking is applied to the wrist area of the subject. Methods to apply dielectric ink markings to the skin are described (see e.g., U.S. Patent App. Pub. No. 2009/0039158, which is incorporated herein by reference). The dielectric ink is applied in a pattern that encodes medical information about the subject and the vaccination. The encoded information may include the subject's name, birthdate, and insurance carrier; the vaccine's identity, lot number, and producer; the date of the vaccination; and the identity of the healthcare giver. The medical information and the corresponding dielectric ink markings are entered into a computer. For example, a dielectric ink is formed from a biocompatible ceramic, sodium potassium niobate ($Na_{0.5}K_{0.5}(NbO3)$)) (see e.g., Bomlai, Proceedings of the Thailand Materials Science and Technology Conference, CO5, 2008, and U.S. Pat. No. 6,526,984, each of which is incorporated herein by reference). Potassium niobate suspended as a fine powder in a fluid solvent, such as water, dimethyl sulfoxide, or 2-propanol, and an inkjet printer may be used to create a pattern that encodes medical information on the skin (see e.g., U.S. Patent App. Pub. No. 2003/0065294, which is incorporated herein by reference). A microwave readable barcode with dielectric elements encoding 96 bits may be printed in a width of approximately 28 mm. Alternatively, for a long-term or permanent marking, the dielectric elements may be injected into the dermis. (See e.g., U.S. Patent App. Pub. No. 2009/0039158, Ibid.).

The dielectric pattern may form a representation (e.g., bar code) made up of bars with varying width, height, vertical distribution, and orientation, or the pattern may form a binary code (e.g., zeros and ones). The dielectric markings are read by irradiation with a microwave transmitter operating at approximately 1.0 TeraHerz frequency and 300 µm wavelength followed by detection of the attenuated portion of the signal resulting after microwaves strike the dielectric elements and scattering occurs.

The microwave signal is detected by a sensor that may be an antenna connected to the microwave transmitter. The sensor also includes a processor capable of decoding the encoded information present in the dielectric pattern. The information processed by the sensor is transmitted to a computer for storage and analysis. Systems for detecting dielectric barcodes are described (see e.g., U.S. Patent App. Pub. No. 2009/0039158, Ibid.). The dielectric pattern printed on the subject at the time he or she received a flu vaccine may be interrogated remotely by a sensor, and the information obtained may be transmitted to a third party.

Compliance with a recommended vaccination schedule may be rewarded by a third party. For example, an insurance company may receive information from a remote dielectric marking sensor in a clinic waiting room or in a public place (e.g., airport, shopping mall), certifying that a subject has received an influenza vaccination. The insurance company may reward the subject by providing a credit to the subject's credit card for any medical bills incurred in the clinic. Alternatively, the insurance company may reward the subject by awarding credits at the shopping mall or travel miles on the patient's credit card.

The vaccination history and reward history for the subject are stored in a database in the system's computer, and are updated when new vaccinations, new dielectric markings, and new rewards are detected by handheld sensors. Detection may occur at the time of new vaccination or later, for example by a remote sensor in a public place. The stored information may be used by a third party, for example by an insurance company for billing purposes, or by an insurance company or public health system for statistical purposes.

Prophetic Example 6

Spectral Medical Information Mark

A patient is vaccinated and a device is used to record medical information in the skin of the patient. The device is an adherent patch with an array of microneedles containing phosphors and fluors which encode information in the patient's skin when the device is applied to the injection site. Phosphors with different emission spectra and phosphorescence time constants are applied in a pattern to the patient's skin which is detected by illumination and detection of fluorescence and phosphorescence to read the encoded information. A CCD camera is used to image the time resolved phosphorescent light and the optical data are transmitted to a computer to translate the encoded medical information. Optically encoded medical information confirming the vaccination may be transmitted to a third party, e.g., an insurance company, to trigger a reward for the patient.

A child is injected with vaccines using standard procedures and a pattern of phosphorescent and fluorescent nanoparticles is administered using a microneedle array patch immediately following vaccination. See, for example, FIG. 6. For example, a combination vaccine for measles, mumps and rubella is injected subcutaneously in the arm of the child, according to the manufacturers' instructions (e.g., see M-M-R® II Product Sheet: available from Merck and Co., Inc., Whitehouse Station, N.J. which is incorporated herein by reference). Immediately following vaccination, the patch with an array of microneedles containing phosphorescent and fluorescent nanoparticles is applied at the vaccination site to record medical information about the vaccination. Nanoparticles containing fluorescent and phosphorescent molecules are deposited approximately 50 μm to 500 μm below the skin surface in the epidermis.

Phosphorescent and fluorescent nanoparticles which absorb and emit light are prepared with targeting molecules on their surface to promote retention in the epidermis. For example, nanoparticles with a phosphorescent dye, platinum (II)-tetraphenyltetranaphthoporphyrin (PtTPNP) encapsulated in diacyllipid-poly (ethylene glycol) micelles are prepared with membrane antibodies specific for alpha-keratin on their surface. Methods and chemicals to prepare PtTPNP encapsulated in phospholipid micelles are described (see e.g., Kumar et al., ACS Applied Materials and Interfaces 7: 1474-1481, 2009 which is incorporated herein by reference). Nanoparticles with a mean hydrodynamic diameter of approximately 100 nm and an absorption maximum at approximately 691 nm and an emission maximum at approximately 903 nm may be prepared using PtTPNP and phospholipids containing 20% of 1,2-distearoyl-sn-glycero-3-phosphoethanolamine-N-[methoxy(polyethylene glycol)-2000] (DSPE-mPEG-2000), 20% of 1,2-distearoyl-sn-glycero-3-phosphoethanolamine-N-[amino(polyethylene glycol)-2000] (DSPE-PEG-2000 NH2), and 60% of 1,2-distearoylglycero-3-phosphocholine (DSPC) (all are available from Avanti Polar Lipids, Inc., Alabaster, Ala.).

Alternate phosphors with different absorption and emission maxima may be encapsulated in liposomes. For example, a palladium (II) complex of 6-Aza-13,20,27-triphenyltetrabenzoporphyrin (PdNTBP) has an absorption maximum at 642 nm and an emission maximum at 875 nm. Preparation of PdNTBP complexes and nanoparticles is described (see e.g., Borisov et al., ACS Applied Materials and Interfaces 2: 366-374, 2010 which is incorporated herein by reference). Furthermore, methods and chemicals to create mixtures of phosphors and fluorophores which display different absorption and emission wavelength maxima are described (see e.g., U.S. Pat. No. 7,910,022, which is incorporated herein by reference). For example, a mixture of fluorophores (e.g., rhodamine 19P, dichlorofluorescein, Nile Blue, Nile Red, sulfarhodamine B, rhodamine 800, diethyloxatricarbocyannine iodide (all available from Sigma-Aldrich, St. Louis, Mo.)) and a phosphor (H13 green phospor available from Capricorn Specialty Chemicals, Ely, U.K.) are combined to produce a photoluminescent mix with an emission maximum at 720 nm and absorption maxima in the visible range (see e.g., U.S. Pat. No. 7,910,022 Ibid.). Nanoparticles containing different phosphors and/or mixtures of phosphors and fluorophores with distinct emission maxima and distinct phosphorescent lifetimes are encapsulated in phospholipid micelles which also have membrane antibodies specific for an epidermal antigen on their surface to target the nanoparticles to the epidermis.

A membrane antibody specific for alpha-keratin, an epidermal antigen, is produced using recombinant DNA methods and inserted in the phospholipid micelles. Human immunoglobulin (Ig) genes encoding a membrane IgG antibody specific for alpha-keratin may be obtained from an antibody phage display library (see e.g., de Haard et al., J. Biol. Chem. 274: 18218-18230, 1999 which is incorporated herein by reference). The Ig genes encoding an anti-keratin membrane Ab are expressed in a mammalian cell line and the membrane antibody is purified from the cell line. For example, a kappa (κ) L chain gene and a γ-1 H chain gene are inserted in a lentiviral expression vector using standard recombinant DNA methods (see e.g., U.S. Patent Publication No. 2007/0116690, which is incorporated herein by reference). The viral vector is used to transfect Chinese Hamster Ovary (CHO) cells (available from American Type Culture Collection, Manassus, Va.) which are engineered to express membrane Ig. Methods to express membrane Ig are known (see e.g., Price et al., J. Immunol. Methods 343: 28-41, 2009 which is incorporated herein by reference). To identify and isolate CHO clones expressing the anti-alpha-keratin antibody a phycoerythrin-conjugated anti-human IgG Ab is used to label CHO cells and sort them using FACS (see e.g., Price et al., Ibid.). A CHO cell line producing anti-alpha-keratin membrane IgG is isolated and expanded. While membrane IgG is purified from CHO cell lysates using an immunoaffinity column. An affinity column constructed from protein A-Sepharose (available from Sigma-Aldrich Co., St. Louis, Mo.) is used to purify membrane IgG from lysates of the engineered CHO cells. For example cells may be lysed in a buffer containing: 0.15 M NaCl, 0.01 M TrisHCl, pH 8.2, 1 mM EDTA, 2 mM phenylmethylsulfonyl fluoride, 0.5% Nonidet P-40 and 1 mg/mL HSA (see e.g., Schneider et al., J. Biol. Chem. 257: 10766-10769, 1982 which is incorporated herein by reference). The purified anti-alpha-keratin membrane IgG is used to construct liposomes which are fused to the phospholipid micelles containing phosphorescent and fluorescent molecules. Methods to fuse liposomes using electrofusion are known (see e.g., Zimmermann et al., *IEEE Transactions On Plasma Science* 28: 72-82, 2000 which is incorporated herein by reference). To measure anti-alpha-keratin IgG protein on the liposomes they are analyzed on a flow cytometer after staining with FITC-labeled anti-IgG antibody. Liposomes are sorted based on FITC fluorescence, forward scatter and side scatter to isolate and count liposomes with IgG. Anti-alpha-keratin IgG protein on the liposomes is measured using an enzyme-linked immunosorbent assay (ELISA).

Methods to analyze liposomes by flow cytometry and to measure IgG and other proteins by ELISA are known (see e.g., U.S. Patent Application No. 2005/0208120, which is incorporated herein by reference).

Following vaccination, a patch with an array of microneedles containing phosphorescent nanoparticles is applied to the skin at the site of the vaccination. An array of microneedles which dissolve and deliver phosphorescent nanoparticles when inserted in the skin is fabricated from carboxymethylcellulose (CMC). Methods and chemicals to fabricate microneedle arrays with encapsulated fluorophores are described (see e.g., Lee et al., Biomaterials 29: 2113-2124, 2008 which is incorporated herein by reference). For example, microneedle arrays (10×8) containing 80 microneedles in an area of approximately 20×20 mm are constructed with pyramidal microneedles approximately 600 μm in length, and a base width of approximately 300 μm. Liposome encapsulated nanoparticles containing a phosphor, e.g., PtTPNP, are suspended in CMC to form a hydrogel which is spin cast into a mold to form the microneedle array. A subset of microneedles in the array may be cast with CMC containing a different phosphor, e.g., PdNTBP, or with CMC without a phosphor to encode information in the array. The microneedle array with encoded information is attached to an adhesive bandage and applied to the vaccine injection site. Thumb pressure on the back side of the microneedle array inserts the microneedles into the skin where they dissolve releasing the liposomes within approximately 15 to 60 minutes. Liposomes with phosphorescent nanoparticles are deposited to a depth of approximately 150-200 μm in the epidermis where they bind to alpha-keratin by virtue of membrane antibodies on the surface of the liposomes (see above).

The microneedle array is encoded with medical information about the vaccine, the date of the vaccination, and patient information. For example, if a patient who is 12 months old receives the M-M-R® II vaccine and requires a future vaccination with M-M-R® II vaccine in 3 to 5 years, the information is entered into a computer, and then encoded in the microneedle array by microcircuitry which selects the phosphors and array pattern to encode the medical information. For example, microneedles in row 1, positions 1-8, on the array are formulated with PtTPNP (with an emission maximum at approximately 900 nm) or PdNTBP (with an emission maximum at 875 nm) or no phosphor to create a code ($3^8$ or approximately 6,500 unique codes are possible) which may indicate the vaccine name. Succeeding rows (2-10) are encoded to indicate the vaccine lot number, vaccination date, clinic, caregiver and information about the patient including name, age, future vaccination dates, and insurance identification number.

The array of phosphorescent nanoparticles embedded in the skin of the patient is read by time-resolved phosphorescent imaging. For example, time resolved emission microscopy may be used to image a phosphorescent nanoparticle array in the skin. Methods and photonic equipment to image phosphorescent probes in live cells are described (see e.g., Botchway et al., *Proc. Natl. Acad. Sci. USA* 105: 16071-16076, 2008 which is incorporated herein by reference). Pulsed laser excitation of the phosphors at approximately 690 nm (PtTPNP) or approximately 642 nm (PdNTBP) is accomplished with red laser diodes at the corresponding wavelengths (available from Roithner Lasertechnik GmbH, Vienna, Austria) and emitting with a pulse length of approximately 0.6 nanoseconds.

Time-resolved images are obtained with a time-gated CCD camera, which allows a series of images to be recorded at different time delays after the excitation pulse. For example a subnanosecond-gated intensified CCD camera (available from Andor Technology, South Windsor, Conn.) is synchronized to the laser to collect 0.02 second exposures at increasing intervals after the excitation pulse. Images acquired approximately 100 nanoseconds following excitation may be used to avoid autofluorescence which displays a shorter time constant or to discriminate different phosphors and fluorophores with different time constants. Image data from the nanoparticle array is transmitted to a central computer where the medical information is decoded and stored in the patient's electronic medical record.

Prophetic Example 7

Magnetic Tattoos for Recording and Rewarding Vaccination

A subject is vaccinated with an influenza vaccine, and a marking is made in the skin with a magnetic ink to identify the subject and to record the vaccination. The magnetic ink is detected using a magnetic field sensor. Signals from the sensor are relayed to a computer and analyzed to verify the subject has been vaccinated, and is entitled to a reward. The device and methods are useful for monitoring adherence to a treatment plan, to plan additional vaccinations, and/or to activate a reward system for compliance with the vaccination protocol.

An elderly subject is vaccinated with a seasonal influenza vaccine and marked with a magnetic ink to record medical information in the skin about the vaccine. The vaccine is injected with a microneedle as described (See e.g., Holland et al., *J. Inf. Dis.* 198: 650-658, 2008, which is incorporated herein by reference). Vaccines may be inactivated split-virion influenza vaccines that are formulated according to strain recommendations (e.g., A/New Caledonia/20/99 [H1N1], A/Wellington/1/2004 [H3N2], and B/Jiangsu/10/2003), from monovalent lots used to prepare the licensed vaccine Vaxigrip (Sanofi Pasteur, Swiftwater, Pa.). The intradermal vaccines, are produced by Sanofi Pasteur, (Swiftwater, Pa.) and contain approximately 15 to 21 μg of hemaglutinin (HA) per strain per 0.1-mL dose, and are administered in the deltoid region using the BD Microinjection System (Becton Dickinson, Franklin Lakes, N.J.).

Immediately after microinjection of the influenza vaccines, a magnetic ink marking is applied to the wrist area of the subject. Magnetic inks for marking the skin are described (see e.g., U.S. Pat. No. 7,344,587 issued to Khan et al. on Mar. 18, 2008.) For example magnetic ink may contain magnetic particles which are approximately 1-5 micrometers in diameter and comprised of magnetite ($Fe_3O_4$) and other elements (e.g., nickel, zinc, and manganese) plus a chromophore (e.g., FD&C Blue No. 1) and a biocompatible outer coating or shell (e.g., Epo-Tek® available from Epoxy Technology, Billerica, Mass.). Methods and materials to make magnetic particles which remain in the skin and do not diffuse are described (see e.g., U.S. Pat. No. 6,013,122 issued to Klitzman et al. on Jan. 11, 2000 which is incorporated herein by reference). Moreover the magnetic particles may be designed and produced with selected magnetic properties to encode information and to allow erasure and rewrite of information encoded in the magnetic ink. For example, methods and materials to make magnetic particles with different magnetic moments ranging from approximately $2\mu_B$ to $5\mu_B$ are described (see e.g., Lee et al., "Artificially engineered magnetic nanoparticles for ultra-sensitive molecular imaging," *Nature Medicine* 13: 95-99, 2007 which is incorporated by reference herein.) Also, to allow modification or erasure of information encoded by magnetic particles, they may be constructed with different Curie temperatures. Magnetic powders with a Curie temperature between approximately −50° C. and 150° C. are described (see e.g., U.S. Pat. No. 6,731,111 issued to Sawa et al. on May 4, 2004 which is incorporated herein by reference.) For example, a magnetic powder composition, $Ni0_{0.2}Zn_{0.8}Fe_2O_4$, with a mean particle diameter of 50 nm has a Curie temperature of 40° C. Images (e.g., bar codes) printed with the magnetic particles display little or no magnetic signal after heating at 60° C. (see e.g., U.S. Pat. No. 6,731,111 Ibid.). After erasure magnetic fields may be reestablished in the magnetic ink particles by lowering the temperature below 40° C. and applying an external magnetic field.

Also, magnetic ink comprised of magnetic particles with different Curie temperatures, differing permeability and saturation remanence may be used to create indicator markings that indicate erasure and magnetic field induction events. For example, magnetic ink comprised of two magnetic particles: 1) $Ni0_{0.2}Zn_{0.8}Fe_2O_4$, with a mean particle diameter of 50 nm, Curie temperature of 40° C., and 2) $Ni0_{0.25}Zn_{0.75}Fe_2O_4$, with a mean particle diameter of 70 nm, and a Curie temperature of 80° C. displays a reduced magnetic field signal following heating at 60° C. (due to loss of the magnetic field from the particles with Curie temperature of 40° C.). The reduced magnetic signal from the indicator reveals the magnetic markings have been erased (see e.g., U.S. Pat. No. 6,731,111 Ibid.).

Moreover, a magnetic field sensor creates a record including the time and date when the magnetic markings have been erased which is transmitted to a mobile device or a remote computer. Erasure and magnetic field marking events may be used to indicate vaccinations completed or booster vaccinations completed. Magnetic marking events may also be programmed on the patient's medical record to alert the patient and caregiver when a vaccination or booster vaccination is needed. Magnetic inks containing magnetic particles with defined magnetic properties (see above), chromophores and coatings may be used to create rewriteable markings in the skin which encode personal and medical information.

The magnetic ink is applied in a pattern that encodes medical information identifying the subject, the vaccine and the caregiver. The encoded information may include: the subject's name, birthdate, and insurance carrier; the vaccine's identity, lot number and producer; and the date of the vaccination, and the identity of the healthcare giver. The medical information and the corresponding magnetic ink markings are entered into a computer. An inkjet printer may be used to create a pattern that encodes medical information on the skin (see e.g., U.S. Patent Application No. 2003/0065294, which is incorporated herein by reference). The magnetic ink pattern may form a representation (e.g., bar code) made up of bars with varying width, height, vertical distribution, and orientation of bar elements, or the pattern may form a binary code (e.g., zeroes and ones). The magnetic ink markings are read using a magnetic field sensor to detect the magnetic particles and transduce electrical signals to a computer and/or mobile computing device.

An image of the magnetic ink markings is read by a magnetic field sensor which scans the magnetic markings and conveys electrical signals to a mobile computing device. Magnetic field sensors for detecting magnetic ink images and recognizing characters are described (see e.g., U.S. Pat. No. 7,145,330; and U.S. Pat. No. 4,315,246; which are each incorporated herein by reference). For example a scanning magnetic field sensor constructed with magnetic tunneling junction (MTJ) sensor units, a translation apparatus and a data processor may be used to detect magnetic characters. MTJ devices with a multilayer structure and a barrier thickness of approximately 0.5-2.0 nm display a large frequency range (approximately 0-10 GHz) and excellent frequency response to generate dynamic magnetic images are incorporated. MTJ devices comprised of (Fe—Ni)/$Al_2O_3$/Co exhibit magnetoresistance ratios of 28% with a magnetic field of few Oe (Oersted). The sensor may contain 3 MTJ sensor units arranged to measure magnetic field components in the x, y and z dimensions. A sensitivity of 60 mV/G may be achieved. Detailed methods and materials to fabricate magnetic field sensors using optical lithography or electron beam lithography are described (see e.g., U.S. Pat. No. 7,145,330 Ibid.). In addition the magnetic field sensor may have a CCD camera for visual detection of the magnetic ink particles containing chromophores (e.g., FD&C Blue No. 1). The optical image visualized with the CCD camera may be used to center the magnetic field sensor on the magnetic ink markings. The magnetic and optical images may be superimposed to verify the patterns visualized and to obtain the information encoded in both the magnetic and optical properties of the markings.

The magnetic field sensor also includes a processor capable of decoding the information present in the magnetic markings. The information processed by the sensor is transmitted to a computer for storage and analysis. The magnetic pattern printed on the subject at the time he or she received a flu vaccine may be interrogated by a magnetic field sensor at an airport or hospital or other public place, and the information obtained may be transmitted to a third party.

Compliance with a recommended vaccination schedule may be rewarded by a third party. For example, an insurance company may receive information from a magnetic field sensor in a clinic waiting room or in a public place (e.g., airport, shopping mall), certifying that a subject has received an influenza vaccination. The insurance company may reward the subject by providing a credit to the subject's credit card for any medical bills incurred in the clinic. Alternatively, the insurance company may reward the subject by awarding credits at the shopping mall or travel miles on the patient's credit card. The vaccination history and reward history for the subject are stored in a database in the system's computer, and updated when new vaccinations, new magnetic markings, and new rewards are detected by magnetic field sensors, whether at the time of vaccination, or later at other sites.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A programmable device, comprising:
a housing;
at least one first chamber within the housing containing at least one composition of an information mark;
at least one second chamber within the housing containing at least one therapeutic agent, wherein the at least one composition of the information mark of the at least one first chamber corresponds to a specific therapeutic agent of the at least one second chamber;
one or more laser sensors configured for sensing a previously administered information mark of a subject;
at least one magnetic field guide operably coupled to the one or more laser sensors, and configured to physically manipulate the at least one magnetic particle embedded in the skin of the subject;
at least one delivery mechanism including at least one needle operably coupled to the at least one first chamber and the at least one second chamber, and also operably coupled to one or more microprocessors configured to process sensed data from the one or more laser sensors, and actuate the needle of the delivery mechanism to administer to a subject a second information mark composition or pattern of delivery corresponding to a specific therapeutic agent, based on the sensed data of the previously administered information mark of the subject;
wherein each of the previously administered information mark and the second information mark includes at least one magnetic particle and represents one or more characteristics related to the at least one therapeutic agent.

2. The programmable device of claim 1, further including at least one transmitter, receiver, or transceiver.

3. The programmable device of claim 2, wherein one or more of the at least one transmitter, receiver, or transceiver is in communication with at least one computer system.

4. The programmable reader device of claim 3, further including a comparator configured to compare at least one of the type, quantity, or timing of the therapeutic agent delivery to the subject with the type, quantity, or timing prescribed to the subject by a health care worker.

5. The programmable device of claim 2, wherein one or more of the at least one transmitter, receiver, or transceiver is wireless.

6. The programmable device of claim 1, further including a guide configured to steady the device.

7. The programmable device of claim 6, wherein the guide includes at least one of a bi-pod, tri-pod, roller ball, fluid leveling gauge, or mechanical leveler.

8. The programmable device of claim 1, wherein the therapeutic agent includes a vaccine.

9. The programmable device of claim 1, further including one or more components configured for physically or chemically modifying or erasing information associated with the information mark subsequent to being administered to a subject.

10. The device of claim 1, further including at least one of phosphorescent particles, multi-spectral ink, or fluorescent particles.

11. A programmable device, comprising:
a housing;
at least one first chamber within the housing containing at least one composition of an information mark;
at least one second chamber within the housing containing at least one therapeutic agent, wherein the at least one composition of the information mark of the at least one first chamber corresponds to a specific therapeutic agent of the at least one second chamber;
one or more laser sensors configured for sensing a previously administered information mark of a subject;
at least one magnetic field guide operably coupled to the one or more laser sensors, and configured to physically manipulate the at least one magnetic particle embedded in the skin of the subject;
at least one delivery mechanism including at least one needle and operably coupled to the at least one first chamber and the at least one second chamber, and also operably coupled to one or more microprocessors configured to process sensed data from the one or more laser sensors, and actuate the needle of the delivery mechanism to administer to a subject a second information mark composition or pattern of delivery corresponding to a specific therapeutic agent, based on the sensed data of the previously administered information mark of the subject;
at least one transmitter configured to transmit the sensed data to at least one other computing system;
wherein each of the previously administered information mark or the second information mark includes at least one magnetic particle, and represents one or more characteristics related to the at least one therapeutic agent.

12. The device of claim 11, further including at least one of phosphorescent particles, multi-spectral ink, or fluorescent particles.

* * * * *